US009404869B2

(12) United States Patent
Keller

(10) Patent No.: US 9,404,869 B2
(45) Date of Patent: Aug. 2, 2016

(54) MULTIVIEW LIGHT-SHEET MICROSCOPY

(71) Applicant: Howard Hughes Medical Institute, Chevy Chase, MD (US)

(72) Inventor: Philipp Johannes Keller, Ashburn, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 166 days.

(21) Appl. No.: 14/049,470

(22) Filed: Oct. 9, 2013

(65) Prior Publication Data

US 2014/0099659 A1 Apr. 10, 2014

Related U.S. Application Data

(60) Provisional application No. 61/711,645, filed on Oct. 9, 2012.

(51) Int. Cl.
*G01N 21/64* (2006.01)
*G01N 21/17* (2006.01)
*A61B 5/00* (2006.01)

(52) U.S. Cl.
CPC ............ *G01N 21/6486* (2013.01); *G01N 21/64* (2013.01); *A61B 5/0071* (2013.01); *A61B 2503/42* (2013.01); *G01N 2021/1736* (2013.01)

(58) Field of Classification Search
None
See application file for complete search history.

(56) References Cited

U.S. PATENT DOCUMENTS

| | | |
|---|---|---|
| 2009/0225413 A1 | 9/2009 | Stelzer et al. |
| 2011/0115895 A1 | 5/2011 | Huisken |
| 2011/0122488 A1* | 5/2011 | Truong .............. G01N 21/6408 359/385 |
| 2011/0134521 A1 | 6/2011 | Truong et al. |
| 2012/0049087 A1* | 3/2012 | Choi et al. ................ 250/459.1 |
| 2012/0099190 A1* | 4/2012 | Knebel et al. ................ 359/385 |
| 2012/0200693 A1 | 8/2012 | Lippert et al. |

OTHER PUBLICATIONS

Hans-Ulrich Dodt, et al., "Ultramicroscopy: three-dimensional visualization of neuronal networks in the whole mouse brain," Nature Methods, vol. 4, No. 4, Mar. 24, 2007, pp. 331-336.
Jan Huisken, et al., "Optical Sectioning Deep Inside Live Embryos by Selective Plane Illumination Microscopy," Science, vol. 305, Aug. 13, 2004, pp. 1007-1009.
Jan Huisken, et al., "Even fluorescence excitation by multi-directional selective plane illumination microscopy (mSPIM)," Optics Letters, vol. 32, Jul. 31, 2007, pp. 2608-2610 (submitted as 15 pages).
Philipp J. Keller, et al., "Reconstruction of Zebrafish Early Embryonic Development by Scanned Light Sheet Microscopy," Science, vol. 322, Nov. 14, 2008, pp. 1065-1069 plus Supporting Online Material totalling 45 pages.
Philipp J. Keller, et al., "Quantitative in vivo imaging of entire embryos with Digital Scanned Laser Light Sheet Fluorescence Microscopy," Current Opinion in Neurobiology, vol. 18, pp. 624-632; 2008 (online Apr. 15, 2009).
Philipp J. Keller, et al., "Fast, high-contrast imaging of animal development with scanned light sheet-based structured-illumination microscopy," Nature Methods, vol. 7, No. 8, Jul. 4, 2010 (online), pp. 637-645 plus Supporting Online Material totalling 35 pages.
Uros Krzic, et al., "Multiview light-sheet microscope for rapid in toto imaging," Nature Methods, vol. 9, 730-733, Advance Online Publication, Jun. 3, 2012, pp. 1-7 plus Supporting Online Material totalling 20 pages.
Philipp J. Keller, et al., "Light sheet microscopy of living or cleared specimens" Current Opinion in Neurobiology, vol. 22, pp. 1-6, 2011.
Thomas A. Planchon, et al., "Rapid three-dimensional isotropic imaging of living cells using Bessel beam plane illumination," Nature Methods, Advance Online Publication, vol. 8, 417-423; Published online Mar. 4, 2011, pp. 1-10 plus Supporting Online Material totalling 34 pages.
Thai V. Truong, et al., "Deep and fast live imaging with two-photon scanned light-sheet microscopy," Nature Methods, Advance Online Publication, vol. 8, 757-760; Published online Jul. 17, 2011, pp. 1-6.
A.H. Voie, et al., "Orthogonal-plane fluorescence optical sectioning: three-dimensional imaging of macroscopic biological specimens," Journal of Microscopy, vol. 170, Pt. 3, Jun. 1993, pp. 229-236.
Khaled Khairy, et al., "Reconstructing Embryonic Development," Genesis, 49, 488-513, published online Dec. 7, 2010, 26 pages.
Raju Tomer, et al., "Shedding light on the system: Studying embryonic development with light sheet microscopy," Current Opinion in Genetics & Development, 21, pp. 1-8, 2011.
Jan Huisken, et al., "Selective plane illumination microscopy techniques in developmental biology," Development, Jun. 15, 2009, 136(12); 1963-1975.
Jeremie Capoulade, et al., "Quantitative fluorescence imaging of protein diffusion and interaction in living cells," Nature Biotechnology, 29, 835-839, published online Aug. 7, 2011.
Jonathan Palero, et al., "A simple scanless two-photon fluorescence microscope using selective illumination," Optics Express, vol. 18, Issue 8, pp. 8491-8498, Apr. 12, 2010.
Jim Swoger, et al., "Multi-view image fusion improves resolution in three-dimensional microscopy," Optics Express, vol. 15, No. 13, Jun. 25, 2007, pp. 8029-8042 (14 pages).
Stephan Preibisch, et al., "Software for bead-based registration of selective plane illumination microscopy data," Nature Methods, 7, 418-419, Jun. 1, 2010.

* cited by examiner

*Primary Examiner* — Renee Claytor
*Assistant Examiner* — Susan E Fernandez
(74) *Attorney, Agent, or Firm* — DiBerardino McGovern IP Group LLC

(57) ABSTRACT

A live biological specimen is imaged by generating a plurality of light sheets; directing the plurality of light sheets along an illumination axis through the biological specimen such that the light sheets spatially and temporally overlap within the biological specimen along an image plane, and optically interact with the biological specimen within the image plane; and recording, at each of a plurality of views, images of the fluorescence emitted along a detection axis from the biological specimen due to the optical interaction between the light sheets and the biological specimen. The temporal overlap is within a time shift that is less than a resolution time that corresponds to a spatial resolution limit of the microscope.

21 Claims, 23 Drawing Sheets
(4 of 23 Drawing Sheet(s) Filed in Color)

MULTIVIEW LIGHT-SHEET MICROSCOPY

CROSS REFERENCE TO RELATED APPLICATION

This application claims priority to U.S. Application No. 61/711,645, filed Oct. 9, 2012, which is incorporated herein by reference in its entirety.

TECHNICAL FIELD

The disclosed subject matter relates to live imaging of biological specimens.

BACKGROUND

Understanding the development and function of complex biological specimens relies critically on our ability to record and quantify fast spatio-temporal dynamics on a microscopic scale. Owing to the fundamental trade-off between spatial resolution, temporal resolution, and photo-damage, the practical approach in biological live imaging has been to reduce the observation of large specimens to small functional sub-units and to study these one at a time.

SUMMARY

In some general aspects, a live biological specimen is imaged by generating a plurality of light sheets; directing the plurality of light sheets along an illumination axis through the biological specimen such that the light sheets spatially and temporally overlap within the biological specimen along an image plane, and optically interact with the biological specimen within the image plane; and recording, at each of a plurality of views, images of the fluorescence emitted along a detection axis from the biological specimen due to the optical interaction between the light sheets and the biological specimen. The temporal overlap is within a time shift that is less than a resolution time that corresponds to a spatial resolution limit of the microscope.

Implementations can include one or more of the following features. For example, an image of the biological specimen can be created by, for each view of the plurality of views, registering the images of the recorded fluorescence, and fusing the registered images into a fused image; registering each of the fused images of all of the plurality of views; and fusing the registered fused images into a final image representative of the image plane of the biological specimen that corresponds to the spatial and temporal overlap of the light sheets within the biological specimen. The recorded fluorescence images can be registered by aligning the images of the recorded fluorescence; and the registered images can be fused by combining the registered images into a single image.

One or more of the biological specimen, the plurality of light sheets, and the plurality of views at which the fluorescence is recorded can be translated relative to each other along a linear axis by incremental steps so that the plurality of light sheets spatially and temporally overlap within the biological specimen along a set of image planes that spans at least a portion of the biological specimen. For each image plane, the fluorescence produced by the biological specimen due to the optical interaction between the light sheets and the biological specimen can be recorded at the plurality of views. The linear axis can be aligned with the detection axis.

One or more of the biological specimen, the plurality of light sheets, and the plurality of recording views can be translated relative to each other along the linear axis by incremental steps by maintaining the position of the plurality of light sheets and the plurality of recording views; and translating the biological specimen along the linear axis.

One or more of the biological specimen, the plurality of light sheets, and the plurality of recording views can be translated relative to each other along the linear axis by incremental steps by maintaining the position of the biological specimen; and translating the plurality of light sheets and the plurality of recording views along the linear axis.

The images of the fluorescence produced by the biological specimen due to the optical interaction between the light sheets and the biological specimen can be recorded by recording one-photon fluorescence produced by the biological specimen. Each light sheet can be generated by generating a continuous wave light sheet, and the plurality of light sheets can be shuttered so that each light sheet arrives at a distinct point in time at the biological specimen but still within the temporal overlap.

The images of the fluorescence produced by the biological specimen due to the optical interaction between the light sheets and the biological specimen can be recorded by recording two-photon fluorescence produced by the biological specimen. Each light sheet can be generated by generating a pulsed wave light sheet, and directing the plurality of light sheets along the illumination axis through the biological specimen such that the light sheets spatially and temporally overlap within the specimen along the image plane comprises activating the light sheets in synchrony.

The images of the fluorescence can be recorded at the plurality of views by recording along the detection axis that is perpendicular to the illumination axis.

The resolution time can correspond to spatial displacements in the structure of the biological specimen that are on the order of the spatial resolution limit of the microscope.

A minimal thickness of each of the light sheets taken along the detection axis can be less than a cross sectional size of a structure within the specimen to be imaged.

In another general aspect, a microscope system for imaging of a live biological specimen includes a specimen holder on which the biological specimen is mounted; a plurality of illumination subsystems; a plurality of detection subsystems; and a translation system. Each illumination subsystem includes a light source and a set of illumination optical devices arranged to produce and direct a light sheet toward the biological specimen, and a set of actuators coupled to one or more illumination optical devices. Each detection subsystem includes a camera and a set of detection optical devices arranged to collect and record images of fluorescence emitted from the biological specimen, and a set of actuators coupled to one or more of the camera and the detection optical devices. The translation system is electro-mechanically coupled to one or more of the specimen holder, the plurality of illumination subsystems, and the plurality of detection subsystems, and configured to translate one or more of the biological specimen, the plurality of light sheets, and the plurality of detection subsystems relative to each other along a linear axis without rotating the biological specimen.

Implementations can include one or more of the following features. For example, the microscope system can include a control system connected to the plurality of illumination subsystems, the plurality of detection subsystems, and the translation system, and configured to send signals to the translation system to translate the specimen holder relative to the plurality of illumination subsystems and the plurality of detection subsystems along a linear axis that is parallel with a normal to a set of image planes; for each image plane, send signals to the plurality of illumination subsystems to cause the light sheets from each of the plurality of illumination subsystems to spatially and temporally overlap within the biological specimen along the image plane to thereby optically interact with the biological specimen; and for each image plane, receive signals from the plurality of detection subsystems acquiring the fluorescence emitted from the biological specimen. The temporal overlap is within a time shift that is less than a resolution time that corresponds to a spatial resolution of the microscope system.

Each of the plurality of detection systems can be arranged along a respective detection axis that is perpendicular to the illumination axis.

In other general aspects, a live biological specimen is imaged using a light sheet microscope by generating a plurality of light sheets; directing the plurality of light sheets along an illumination axis through the biological specimen such that the light sheets spatially and temporally overlap within the biological specimen along an image plane; recording, at a plurality of views, images of the fluorescence produced by the biological specimen due to the interaction between the biological specimen and the light sheets; and creating an image of the biological specimen. The image is created by, for each view of the plurality of views, aligning the recorded images; and combining the aligned images into a fused image. Additionally, the image is created by aligning the fused images from all of the plurality of views; and combining the aligned fused images into a final image representative of the image plane of the biological specimen that corresponds to the spatial and temporal overlap of the light sheets within the biological specimen.

Implementations can include one or more of the following features. A minimal thickness of each of the light sheets taken along a z axis, which is perpendicular to the illumination axis and overlaps the illumination axis along which the fluorescence is recorded, can be less than a cross sectional size of a structure within the specimen to be imaged.

The microscope system provides a useful tool for the in vivo study of biological structure and function at a level that captures an entire complex biological specimen. It includes a light sheet microscopy technique that is based on the idea of illuminating the biological specimen or sample with a thin sheet of laser light that is directed along a light axis, and recording the fluorescence emitted from this thin volume orthogonally to the light axis. The laser light is thin compared with the size of the biological specimen. For example, the thin volume could be about 100 nm to about 10 μm wide in the direction of the light axis.

Only the in-focus part of the biological specimen is exposed to laser light, which provides optical sectioning and substantially reduces photo-damage. Moreover, the fluorescence signal emitted from the in-focus section is detected simultaneously in time for the entire field-of-view, which provides exceptionally high imaging speeds. In comparison to confocal microscopy, a commonly used optical sectioning technique, imaging speed, signal-to-noise ratio and photo-bleaching rates are improved by up to several orders of magnitude. Advances have enabled further breakthroughs in spatial and temporal resolution, as well as in the conceptual design and complexity of live imaging experiments.

The microscope system is able to penetrate more than several tens to hundreds of microns into living tissue, thus enabling systems-level imaging, which is imaging of complex biological specimens or organisms. The microscope system and related process achieve high imaging speeds in the order of 100 frames per second such that dynamic biological processes within the complex specimen can be captured at high spatio-temporal resolution.

The microscope system is fast enough to capture fast processes in live specimens. For example, in live multi-cellular organisms, fast developmental processes can occur between the sequential multiview acquisitions that occur in sequential multiview imaging systems, and this precludes accurate image fusion of the acquired data. The microscope system therefore avoids spatio-temporal artifacts that can fundamentally constrain quantitative analyses, such as the reconstruction of cell tracks and cell morphologies.

For global measurements of the dynamic behavior and structural changes of all cells in a complex developing biological specimen or organism, data acquisition occurs at speeds that match the time-scales of the fastest processes of interest and with minimal time shifts between complementary views.

The technology framework for simultaneous multiview imaging with one-photon or multi-photon light sheet-based fluorescence excitation is designed to deliver exceptionally high imaging speeds and physical coverage while minimizing or reducing photo-bleaching and photo-toxic effects. The microscope system excels at the quantitative in vivo imaging of large biological specimens in their entirety, over long periods of time and with excellent spatio-temporal resolution.

Similar to its implementation with two-photon excitation, the concept can also be combined with Bessel plane illumination, scanned light sheet-based structured illumination or functional imaging approaches, among others. Thus, the "light sheet" used in the illumination subsystems encompasses these other illumination approaches. And, thus, the light sheet could be a scanned light sheet or a static light sheet. The use of laser scanning to generate a light sheet (that is, illuminating only one line in the specimen at a time) enables the use of two-photon excitation and Bessel beam illumination, and the temporal character of the scanning process also allows the construction of complex illumination patterns such as structured light sheets (stripes of light).

The imaging technique presented here opens the door to high-throughput high-content screening, fast functional imaging and comprehensive quantitative analyses of cellular dynamics in entire developing organisms. By combining this method with advanced computational tools for automated image segmentation and cell tracking, the reconstruction of high-quality cell lineage trees, comprehensive mapping of gene expression dynamics, automated cellular phenotyping and biophysical analyses of cell shape changes and cellular forces are within reach, even for very complex biological specimens.

In comparison to single-view imaging, simultaneous multiview imaging improves coverage almost four-fold and reveals cellular dynamics in the entire early embryo. Moreover, in comparison to sequential multiview imaging, simultaneous multiview imaging eliminates or greatly reduces temporal and spatial fusion artifacts during fast nuclear movements, improves temporal resolution, and provides quantitative data for subsequent computational image analysis, such as automated cell tracking. Simultaneous multiview imaging also reduces the energy load on the specimen by avoiding the redundant iterative acquisition of overlapping regions required for sequential multiview image registration.

Besides the elimination of spatial and temporal artifacts, simultaneous multiview imaging also provides excellent temporal resolution. This point can be illustrated with basic parameters quantifying cellular dynamics in the *Drosophila* embryo, as discussed below. For example, fast movements of thousands of nuclei occur during the mitotic cycles in the syncytial blastoderm: In the $12^{th}$ mitotic cycle, the average movement speed of dividing nuclei is 8.12±2.59 μm/min (mean±s.d., n=2,798, Huber robust estimator) and the average nearest neighbor distance is 7.57±1.34 μm (mean±s.d., n=1.44×10$^5$, Huber robust estimator). Importantly, nearest neighbors are usually not daughter nuclei from the same mother nucleus. Hence, in order to obtain quantitative data for the analysis of nuclear dynamics in the entire blastoderm, simultaneous multiview imaging is required at an overall speed that ensures, on average, nuclear movements of no more than half of the nearest neighbor distance between subsequent time points. Simultaneous multiview imaging of the entire embryo therefore has to be performed with at most about 30 second temporal sampling.

DESCRIPTION OF DRAWINGS

The patent or application file contains at least one drawing executed in color. Copies of this patent or patent application publication with color drawing(s) will be provided by the Office upon request and payment of the necessary fee.

FIG. 13B is a maximum-intensity projection of images of the *Drosophila* embryo taken using the one photon excitation scheme at one point in time;

The patent or application file contains at least one drawing executed in color. Copies of this patent or patent application publication with color drawings will be provided by the Office upon request and payment of the necessary fee.

DETAILED DESCRIPTION

Figure 1A:
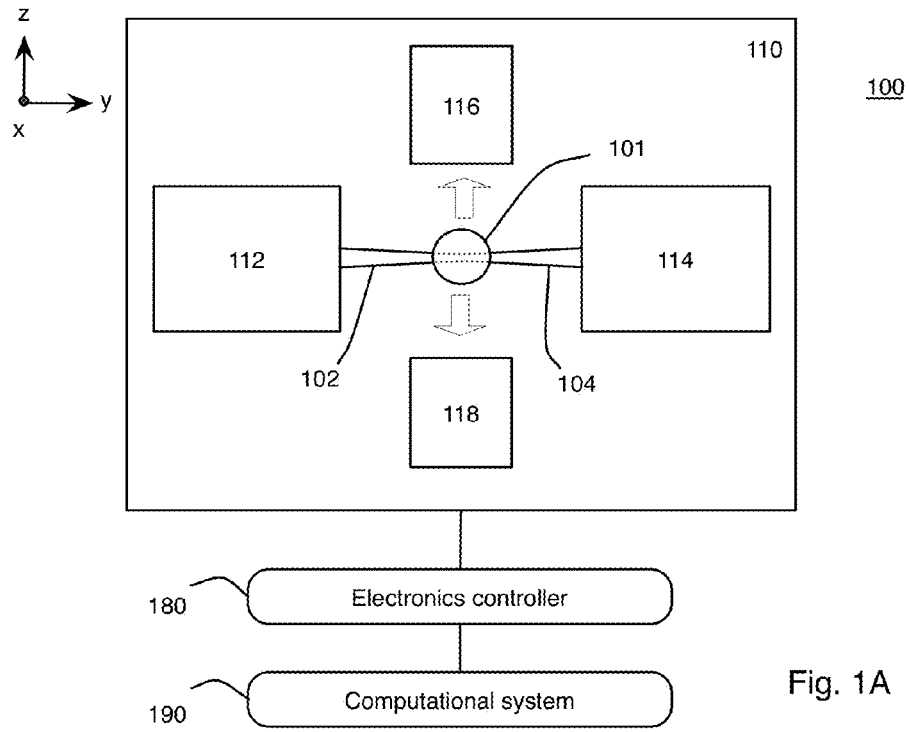
FIG. 1A is a block diagram of an exemplary microscope system that uses light sheet microscopy to provide simultaneous multiview imaging of a biological specimen.

Referring to FIG. 1A, this description relates to a microscope system 100 and corresponding process for live imaging of a complex biological specimen (or specimen) 101, such as a developing embryo, in its entirety. For example, the complex biological specimen 101 can start off as a fertilized egg; in this case, the microscope system 100 can capture the transformation of the entire fertilized egg into a functioning animal, including the ability to track each cell in the embryo that forms from the fertilized egg as it takes shape over a period of time on the scale of hours or days. The microscope system 100 can provide a compilation of many images captured over about 20 hours to enable the viewer to see the biological structures within the embryo that begin to emerge as a simple cluster of cells morph into an elongated body with tens of thousands of densely packed cells.

The microscope system 100 uses light-sheet microscopy technology that provides simultaneous multiview imaging, which eliminates or reduces spatiotemporal artifacts that can be caused by slower sequential multiview imaging. Additionally, because only a thin section (for example, on the order of a micrometer (μm) wide taken along the z axis) of the specimen 101 is illuminated at a time with a scanned sheet of laser light while a detector records the part of the specimen 101 that is being illuminated, damage to the specimen 101 is reduced. No mechanical rotation of the specimen 101 is required to perform the simultaneous multiview imaging.

In general, the optical microscope 110 is made up of a plurality of light sheets (for example, light sheets 102, 104) that illuminate the specimen 101 from distinct directions along respective light sheet axes, and a plurality of detection subsystems (for example, detection subsystems 116, 118) that collect the resulting fluorescence along a plurality of detection views. In the example that follows, two light sheets 102, 104 are produced in respective illumination subsystems 112, 114, which illuminate the specimen 101 from opposite directions or light sheet axes; and the respective detection subsystems 116, 118 collect the resulting fluorescence along two detection views. In this particular example, the light sheet axes are parallel with an illumination axis (the y axis) and the detection views are parallel with a detection axis (the z axis), which is perpendicular to the y axis.

Therefore, in this example, the microscope system 100 provides near-complete coverage with the acquisition of four complementary optical views; the first view comes from the detection system 116 detecting the fluorescence emitted due to the interaction of the light sheet 102 with the specimen 101; the second view comes from the detection system 116 detecting the fluorescence emitted due to the interaction of the light sheet 104 with the specimen 101; the third view comes from the detection system 118 detecting the fluorescence emitted due to the interaction of the light sheet 102 with the specimen 101; and the fourth view comes from the detection system 118 detecting the fluorescence emitted due to the interaction of the light sheet 104 with the specimen 101.

Figure 1B:
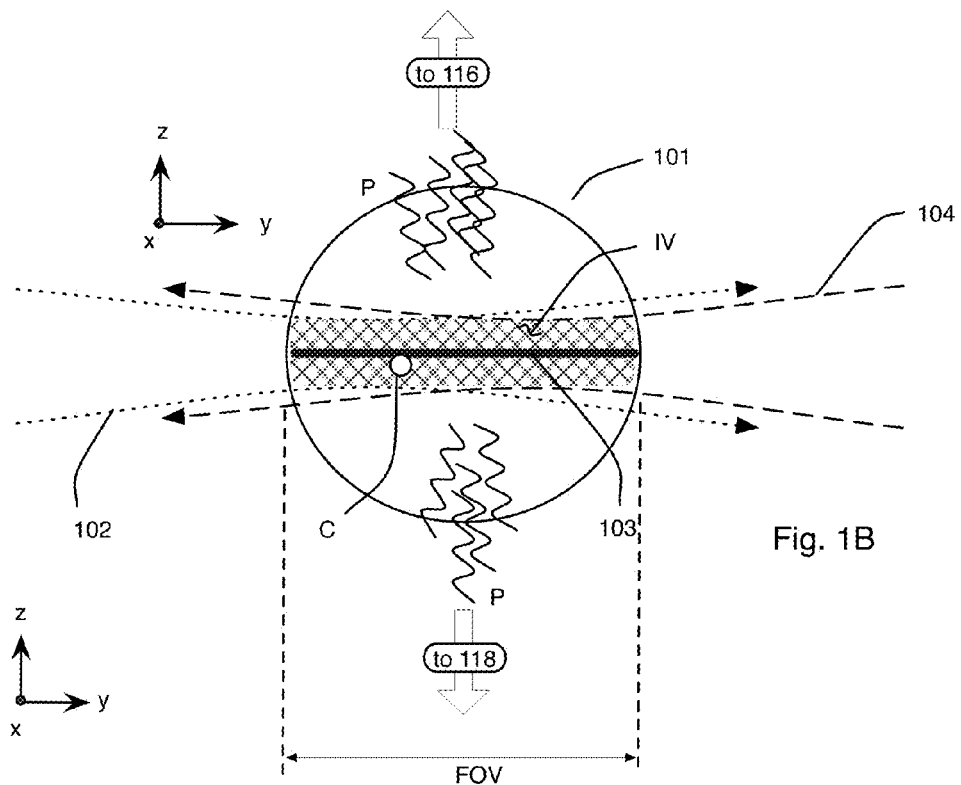
FIG. 1B is a block diagram showing an exemplary schematic representation of the specimen imaged using the microscope system of FIG. 1A.
Figure 2:
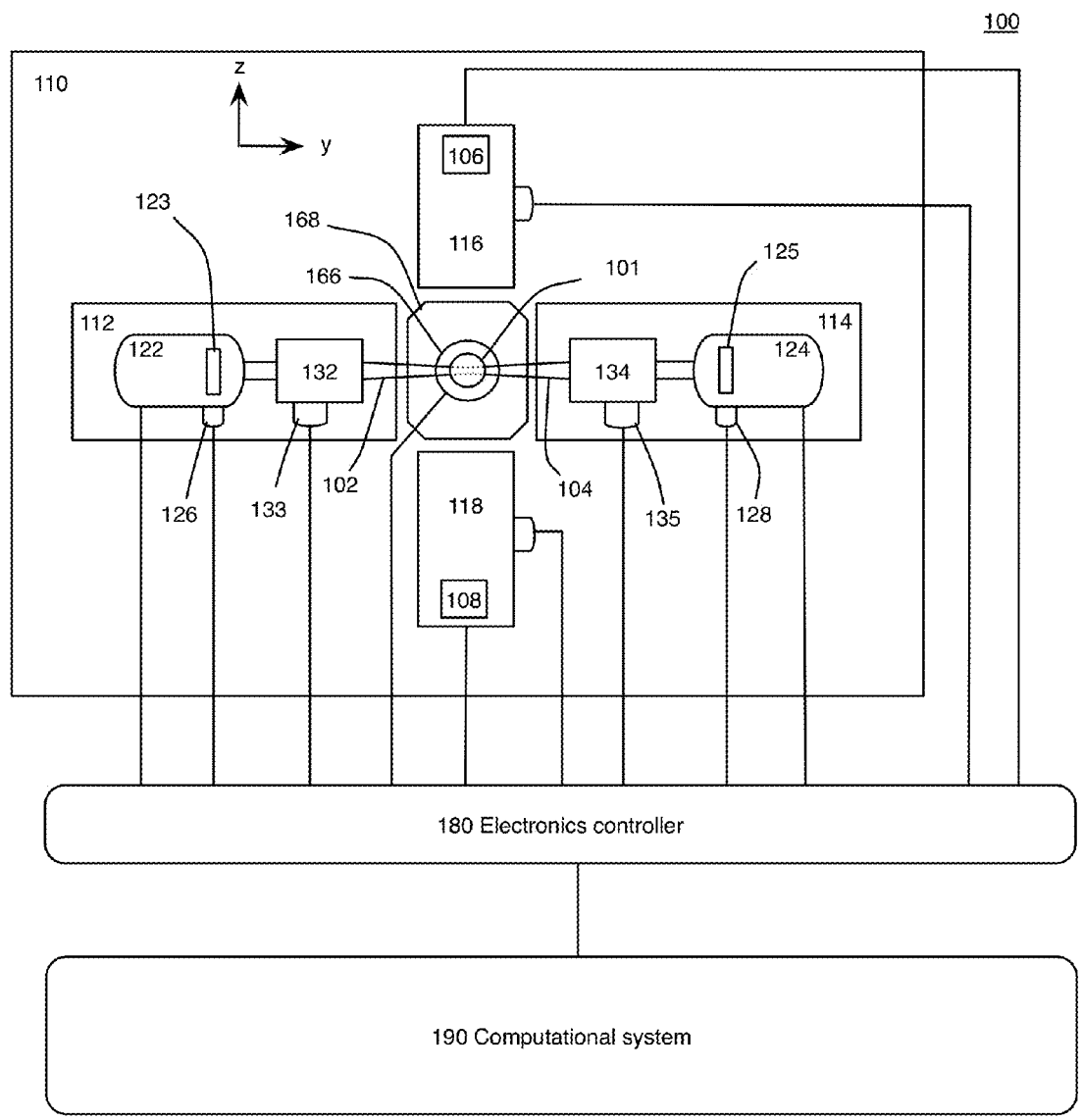
FIG. 2 is a block diagram of an exemplary implementation of the microscope system of FIG. 1A.

Referring to FIG. 1B, which is exaggerated to more clearly show the interactions between the light sheets 102, 104, and the specimen 101, the light sheets 102, 104 spatially overlap and temporally overlap each other within the specimen 101 along an image volume IV that extends along the y-x plane, and optically interact with the specimen 101 within the image volume IV. The temporal overlap is within a time shift or difference that is less than a resolution time that corresponds to the spatial resolution limit of the microscope 110. In particular, this means the light sheets 102, 104 overlap spatially within the image volume IV of the biological specimen 101 at the same time or staggered in time by the time difference, which is so small that any displacement of tracked cells C within the biological specimen 101 during the time difference is significantly less than (for example, an order of magnitude below) a resolution limit of the microscope 110, where the resolution limit is a time that corresponds to a spatial resolution limit of the microscope 110.

As will be discussed in greater detail below, each light sheet 102, 104 is generated with a laser scanner that rapidly moves a thin (for example, μm-thick) beam of laser light along an illumination axis (the x axis), which is perpendicular to the y and z axes, to form a light beam that extends generally along or parallel with a plane to form the sheet 102, 104. In this example, the laser beam in the form of the light sheet 102, 104 illuminates the specimen 101 along the y axis on opposite sides of the specimen 101. Rapid scanning of a thin volume and fluorescence detection at a right angle (in this example, along the z axis) to the illumination axis provides an optically sectioned image. The light sheets 102, 104 excite fluorophores within the specimen 101 into higher energy levels, which then results in the subsequent emission of a fluorescence photon P, and the fluorescence photons P are detected by the detectors within the detection subsystems 116, 118 (along the z axis). As discussed in detail below, in some implementations, the excitation is one-photon excitation, or it is multi-photon (for example, two-photon) excitation.

The fluorophores that are excited in the specimen can be labels that are attached to the cells, such as, for example, genetically-encoded fluorescent proteins such as GFP or dyes such as Alexa-488. However, the fluorophores can, in some implementations that use second-harmonic generation or third-harmonic generation, be actual or native proteins within the cells that emit light of specific wavelengths upon exposure with the light sheets 102, 104.

As shown schematically in FIG. 1B, the light sheets 102, 104 pass through the specimen 101 and excite the fluorophores. However, the light sheets 102, 104 are subject to light scattering and light absorption along their respective paths through the specimen 101. Moreover, very large (large compared with the image volume IV or the field-of-view (FOV)) or fairly opaque specimens can absorb energy from the light sheets 102, 104.

Moreover, if the light sheets 102, 104 are implemented in a two-photon excitation scheme, then only the central region 103 of the overlapping light sheets 102, 104 may have a high enough power density to efficiently trigger the two-photon process, and it is possible that only (the close) half of the specimen 101 emits fluorescence photons P in response to exposure to two-photon light sheets 102, 104.

The term "spatial overlap" of the light sheets could mean that the light sheets 102, 104 are overlaid geometrically within the specimen 101. The term "spatial overlap" can also encompass having the light sheets both arrive geometrically within the FOV (as shown in FIG. 1B) of the detection subsystems 116, 118 and within the specimen 101. For example, to efficiently trigger two-photon excitation, each light sheet 102, 104 could cover only a part of (for example, one half) of the field-of-view of the detection subsystems 116, 118 (so that each light sheet is centered in the respective half of the field-of-view) so that the use of both of the light sheets 102, 104 leads to the full field-of-view being visible.

Because of this, each two-photon light sheet 102, 104 can be made thinner (as measured along the z axis), if the light sheet 102, 104 only needs to cover half of the field-of-view. However, if the light sheet 102, 104 is thinner (and the laser power unchanged), the same number of photons travel through a smaller cross-section of the specimen 101, that is, the laser power density is higher, which leads to more efficient two-photon excitation (which is proportional to the square of the laser power density). At the same time, because the light sheets are thinner, the resolution is increased when compared to a scenario in which each light sheet 102, 104 covers the entire field-of-view.

As another example, if the light sheets 102, 104 are implemented in a one-photon excitation scheme, the light sheet 102, 104 could also excite fluorophores on the area of the specimen 101 outside of the central region 103 but within the image volume, and this part will appear blurrier in the resultant image. In this latter case, two images can be sequentially recorded with each of the two light sheets 102, 104, and the computational system 190 can use a calculation to adjust the images to obtain a higher quality. For example, the two images can be cropped such that the low-contrast regions are eliminated (and complementary image parts remain after this step), and then the images recorded with the two light sheets can be stitched together to obtain a final image that covers the entire field-of-view in high quality.

The light sheet 102, 104 is configured so that its minimal thickness or width (as taken along the z axis) is within the image volume IV and the FOV. When two light sheets 102, 104 are directed toward the specimen 101, then the minimal thickness of the respective light sheet 102, 104 should overlap with the image volume IV. As discussed above, it can be set up so that the minimal thickness of the light sheet 102 is offset from the minimal thickness of the light sheet 104, as shown schematically in FIG. 1B. This set up provides improved or superior spatial resolution (for both one-photon and two-photon excitation schemes) and improved or superior signal rates (for two-photon excitation schemes).

For example, for a specimen 101 that is a *Drosophila* embryo that is about 200 µm thick (taken along the z axis), the light sheet 102 can be configured to reach its minimal thickness about 50 µm from the left edge (measured as the left side of the page) of the specimen 101 after it crosses into the specimen 101 while the light sheet 104 can be configured to reach its minimal thickness about 50 µm from the right edge (measured as the right side on the page) of the specimen 101 after it crosses into the specimen 101.

There is a tradeoff between the minimal thickness of the light sheet 102, 104 and the uniformity of the light sheet 102, 104 thickness across the image volume IV. Thus, if the minimal thickness is reduced, then the light sheet 102, 104 becomes thicker at the edges of the image volume IV. The thickness of the light sheet 102, 104 is proportional to the numerical aperture of the respective illumination subsystem 112, 114; and the useable length of the light sheet 102, 104, that is, the length over which the thickness is sufficiently uniform, is inversely proportional to the square of the numerical aperture. The thickness of the light sheet 102, 104 can be estimated using any suitable metric, such as the full width of the light sheet 102, 104 along the z axis taken at half its maximum intensity (FWHM).

For example, a light sheet 102, 104 having a minimal thickness of 4 µm (using a suitable metric such as the FWHM) is a good match for an image volume IV that has a FOV of 250 µm (which means that it is 250 µm long (as taken along the y axis)). A good match means that it provides a good average resolution across the field of view. A thinner light sheet would improve resolution in the center (taken along the y axis) but could degrade the resolution dramatically and unacceptably at the edges of the specimen 101, and possibly lead to worse average resolution across the field-of-view. A thicker light sheet would make the light sheet more uniform across the image volume IV, but it would degrade the resolution across the entire image volume IV. As another example, a light sheet 102, 104 having a minimal thickness of 7 µm (using a suitable metric such as the FWHM) is a good match for an image volume IV that has a FOV of 700 µm (and thus it is 700 µm long (as taken along the y axis)).

In general, the thickness of the light sheet 102, 104 (as taken along the z axis) should be less than the size (and the thickness) of the specimen 101 to maintain image contrast and reduce out of focus background light. In particular, the thickness of the light sheet 102, 104 should be substantially less than the size of the specimen 101 in order to improve the image contrast over a conventional illumination approach in which the entire specimen 101 is illuminated. Only in this regime (light sheet thickness is substantially smaller than specimen thickness), light-sheet microscopy provides a substantial advantage over conventional illumination approaches.

For example, the thickness of the light sheet 102, 104 can be less than one tenth of the width of the specimen 101 as taken along the z axis. In some implementations, the thickness of the light sheet 102, 104 is on the order of one hundredth of the width or size of the specimen 101 if each light sheet is used to cover only a portion (such as a half) of the field-of-view, that is, the point of minimal thickness of each light sheet is located in the center of one of the two halves of the field-of-view, as discussed above.

Another important consideration for setting the minimal thickness of the light sheet 102, 104 or for defining a realistic image volume IV, is the size of the structure within the specimen 101 that needs to be resolved by the microscope system 100. Often, the microscope system 100 is set up to image cell nuclei, which are about 4-5 µm in size (taken along a straight line across the nucleus) in Drosophila, and around 7-8 µm in size in a zebrafish at the early developmental stages in which the system 100 can be used. To achieve reasonably good spatial sampling and resolution, the light sheet 102, 104 should have a minimal thickness that is not much thicker than half the cross-sectional size or length of these nuclei. Thus, for *Drosophila*, the minimal thickness of the light sheet 102, 104 should be less than 2-3 µm while for the zebrafish, the minimal thickness of the light sheet 102, 104 should be less than 3-4 µm. Moreover, the images of the specimen 101 should be recorded in steps taken along the z axis (by either translating the specimen 101, the light beams 102, 104, or both the specimen 101 and the light beams 102, 104 along the z axis); and the size of the steps should be about the size of this minimal thickness.

The microscope system 100 is a comprehensive solution that includes a complete technology framework. Thus, the microscope system 100 also includes an electronics framework that includes the electronics controller 180 and the computational system 190. The electronics controller 180 provides synchronized control of all opto-mechanical components within the microscope 110 with millisecond precision over long periods of time. The computational system 190 rapidly performs the complex optical alignment on the live specimen 101, and provides a robust pipeline for simultaneous high-speed image acquisition with a plurality of detectors (or cameras) within the detection subsystems 116, 118 at sustained data rates of several hundreds of megabytes per second and a high-throughput computational strategy for efficient automated image processing to register and reconstruct the terabytes of raw multiview image data arising from every experiment.

While the example provided herein describes a four-view system using two light sheets for illumination and two detectors for collecting the fluorescence, more views are possible by adding additional detectors and/or illumination systems. In this example, the illumination subsystems 112, 114 face each other such that the specimen 101 can be illuminated with light sheets from two sides, as more clearly shown in the schematic drawing of FIG. 1B. Each detection subsystem 116, 118 includes a respective detector or camera 106, 108 in addition to a set of detection optical devices arranged to collect and record the fluorescence emitted from the specimen 101. Each detection subsystem 116, 118 also includes a set of actuators that are coupled to one or more of the detector 106, 108 and the detection optical devices at one end and interface at the other end with the electronics controller 180.

Each combination of illumination and detection provides a different view or perspective. By capturing the four views (in this example) simultaneously, delays caused by rotating of the specimen 101 repeatedly into new positions (as in the sequential imaging techniques of past) are reduced or eliminated. Thus, the microscope system 100 is designed for the simultaneous acquisition of multiple complementary views without having the rotate the specimen 101.

Illumination Subsystems

Referring also to FIGS. 2-5A, each of the illumination subsystems 112, 114 includes respective light sources 122, 124 that output respective light beams, and respective sets 132, 134 of optical components that modify properties such as direction, size, geometry, etc. of the light beam to produce the light sheets 102, 104 that are directed to the specimen 101. The light sheets 102, 104 produced within the illumination subsystems 112, 114 can be produced by scanning an output of the respective light sources 122, 124, as will be discussed below.

The light sources 122, 124 can include one or more light sources such as lasers. In some implementations, the light sheets 102, 104 can be generated from a single (one) light source, and then the output from this single light source can be split into two beams to operate as the respective light sources 122, 124. While in other implementations, the light sheets can be generated from two separate light sources that operate as the respective light sources 122, 124.

For a two-photon excitation arrangement, a single pulsed Ti:Sapphire laser can be the sole light source that is split into two beams. In this case, the wavelength of the light can be adjusted to any value between 690 and 1080 nm.

In some implementations of a one-photon excitation arrangement, the light source can be made up of six laser diodes and diode pumped solid state (DPSS) lasers, whose laser beams are all combined on the same optical axis using dichroic mirrors, thus effectively turning the entire unit into something that appears to be a single light source. In this case, there is a benefit to using more than one light source because it provides for multi-color imaging or increased flexibility in fluorescent marker selection. The laser diodes and the DPSS laser each provide a distinct wavelength, and this enables the microscope system 100 to work with different types of fluorescent proteins and even multiple color channels within a single experiment. In some implementations, at any given time, only one wavelength of the arrangement may be activated. The activation of the wavelength can be controlled by the electronics controller 180 and the computational system 190; for example, the electronics controller 180 can send a signal to the lasers or acousto-optical tunable filters, which activate or de-activate the contribution of the respective wavelength within microsecond speed. Since the laser beam is then split into two beams using a static optical element such as a beam splitter, both of the illumination subsystems 112, 114 receive light at the same time; and the fast laser shutters in each subsystem 112, 114 enable selective activation of the light sheets 102, 104 produced in the respective subsystem 112, 114.

In other implementations, a dedicated laser system (or light source) can be provided for each illumination subsystem, and each dedicated laser system could be individually controllable by the electronics controller 180 and the computational system 190.

For example, the light source 122 and the light source 124 can each include one or more solid-state lasers (such as diode-pumped solid-state lasers) that operate at a plurality of wavelengths to provide for flexibility. In one example, each light source 122, 124 includes a SOLE® Laser Light Engine produced by Omicron-Laserage Laserprodukte GmbH of Rodgau-Dudenhofen, Germany. Details on such lights sources can be found at their website at www.omicron-laser.de/. In these Light Engines, a plurality of outputs from internal and individual lasers operating at distinct wavelengths can be combined to form a single output. Outputs from the SOLE® Laser Light Engines can be directed through one or more fiber optics, depending on the application. The light sources 122, 124 are connected to components within the electronics controller 180 to enable the control of the active laser lines and their respective laser power. Additionally, after being combined to form a single output, it is possible to split this output into two illumination arms for fluorescence excitation from near-UV to near-IR, providing the laser wavelengths at, for example, 405 nm, 445 nm, 488 nm, 515 nm, 561 nm, 594 nm, 642 nm, and 685 nm.

In other implementations, it is possible to use a plurality of light sources and/or a plurality of light sheets having different colors at any given time (simultaneously), and equip each detection subsystem 116, 118 with dichroic beam splitters and a plurality of cameras, such that different color channels can be recorded simultaneously.

The output from each of the light sources 122, 124 can be controlled using optical shutters 123, 125, which control the timing of the light sheets 102, 104 that reach the specimen 101, and thus control which of the light sheets 102, 104 (for example, only the light sheet 102, only the light sheet 104, or both the light sheet 102 and light sheet 104) illuminate the specimen 101 at any one moment. In some implementations, the optical shutters 123, 125 are Uniblitz laser shutters (such as Uniblitz LS6ZM2-100 laser shutters or Uniblitz VS14S2ZM1-100 laser shutters). These optical shutters are able to block light that is directed through an aperture, and the blocking of the light can be synchronized, asychronized, or controlled depending on the application. The illumination at the specimen 101 can therefore be performed synchronously or asynchronously from either side. Respective drivers or actuators 126, 128 operate the laser shutters 123, 125 under control from the electronics controller 180. The actuators 126, 128 can be, for example, Uniblitz VMM-D3 three-channel drivers.

Other types of light sources are possible, and the constraints on the selection of the light source include desired wavelength or wavelengths (which can be selected or modified to excite the fluorophores within the specimen 101), desired power, and desired beam quality.

The light beams that are output from the light sources 122, 124 are directed through the respective sets 132, 134 of optical components, which are driven by respective actuator systems 133, 135 that are connected to the electronics controller 180. In general, each set 132, 134 of optical components can include, for example, mirrors, lenses, and objectives, opto-mechanical components (such as objectives) and electro-optical components.

For clarity, the optical component set 132 and its actuator system 133 are described next, and the other optical component set 134 and its actuator system 135 are similarly designed so a separate description of those elements are not provided.

The laser light exits the light source 122 in the illumination subsystem 112 through the optical shutter 123, and is directed to an optical scanner device 140, which deflects the light beam along the x axis to form a light sheet, which is directed toward an f-theta lens 141, a tube lens 142, and an illumination objective 143. The optical scanner device 140 deflects the incident laser light to produce an angular range that defines the height of the light sheet 102 along the x axis in the specimen 101. And, the angle of the light beam that exits the optical scanner device 140 is converted into a displacement along the x axis or direction by the f-theta lens 141 because the optical scanner device 140 is positioned to be located at the focal plane of the f-theta lens 141, thus producing a macroscopic light sheet. The pair of the tube lens 142 and the illumination objective 143 focuses the macroscopic light sheet output from the f-theta lens 141 into the microscopic light sheet 102 at the specimen 101. The illumination objective 143 can be a relatively long working distance air objective.

In this description, the optical scanner device 140 deflects the light beam along the x axis; however, it is possible that the light beam can be deflected along another axis, depending on the application. For example, when performing volumetric imaging without moving the specimen 101, the light beam can be deflected along the z axis too. Moreover, it is possible to deflect or more the light beam along the z axis to align the light sheets 102, 104 with respect to each other.

The optical scanner device 140 can be formed by one or more moveable mirrors 140. The mirrors 140 can be mounted on a tip/tilt stage that is moveable under control of an actuator such as a piezoelectric driver, or they can be integrated within an actuator system such as the S-334 miniature piezo tip/tilt mirror by Physik Instrumente (PI), which includes the mirror. As another implementation, the mirrors 140 can be controlled using galvanometer scanners, such as the model 6215HSM40B from Cambridge Technology. Combining two scanners in an XY scan head provides the same angular degrees of freedom as a tip/tilt mirror assembly, but can be faster.

The piezoelectric driver can be connected to a piezo driver module and a piezo servo module, which are within the electronics controller 180. For example, the PI S-334 can be connected to a PI E-503 piezo amplifier module that includes amplifiers that output current to the piezoelectric actuator to control the movement of the mirror 140 and to a PI E-509 piezo servo module. All of the modules for controlling the mirrors 140 can be housed within a sub-control module within the electronics controller 180.

The f-theta lens 141 converts the tilting movement of the scan mirror 140 into a displacement (shown by the arrow in FIG. 5A) of the laser beam along the x axis. The tube lens 142 and the illumination objective 143 focus the laser beam into the specimen 101, which is aligned with the detection subsystems 116, 118 along the z axis in this example. The f-theta lens 141 can be, for example, a color-corrected lens such as part S4LFT4375 from Sill Optics, which operates for light having a wavelength between 450 nm and 650 nm. The tube lens 142 and the illumination objective 143 can be purchased off the shelf from suppliers such as Carl Zeiss, Nikon, or Olympus. In one example, the tube lens 142 is an Olympus U-TLU-1-2 camera tube lens and the illumination objective 143 is an Olympus XLFLUOR 4x/340/0.28 objective mounted on a piezoelectric positioner that is controlled by electronics within the electronics controller 180. For example, the illumination objective 143 can be mounted to a long-travel scanner such as the P-725 PIFOC produced by Physik Instrumente, which is controlled by an amplifier/servo controller, such as the E-665 produced by Physik Instrumente, within the electronics controller 180.

Additionally, while not shown, the light beams that are output from the light sources 122, 124 can be directed through optical respective filters, which can be mounted on a compact illumination filter wheel with controller (such as a DC servo controller made by Ludl Electronics Products Ltd. of Hawthorne, N.Y.).

In some implementations, the electronic components required to operate all elements in the illumination subsystem 112 can be controlled by a first set of components within the electronics controller 180, while the electronics components required to operate all the elements in the illumination subsystem 114 can be controlled by a second set of components within the electronics controller 180. The selection of the specific optical components in the sets 132, 134 depend on the wavelength of the light that must be passed and directed, the power at which the light operates, and other factors such as numerical aperture or size of focus.

Detection Subsystems

Figure 3:
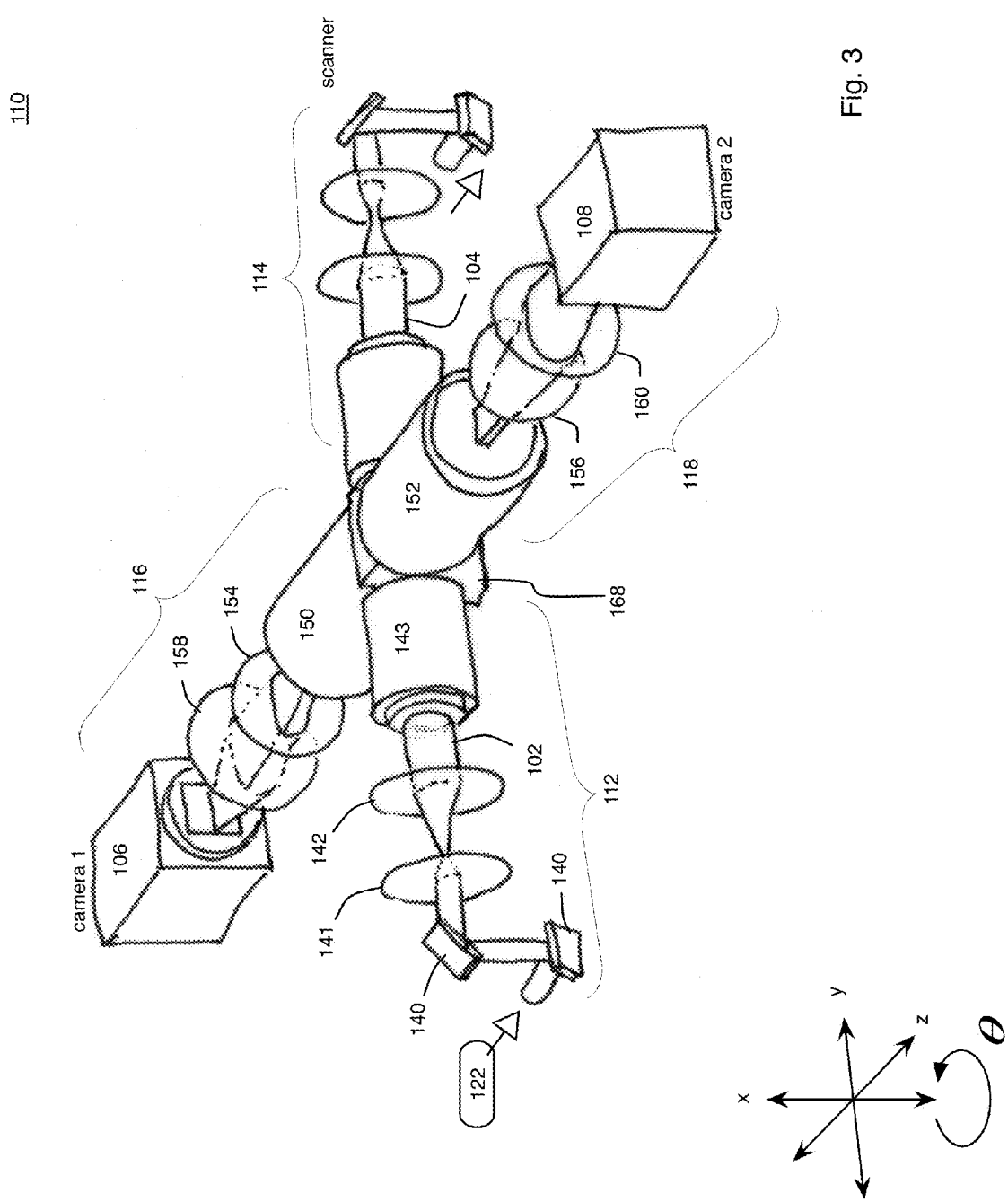
FIG. 3 is a perspective view of an exemplary microscope of the microscope system of FIG. 1A.
Figure 4:
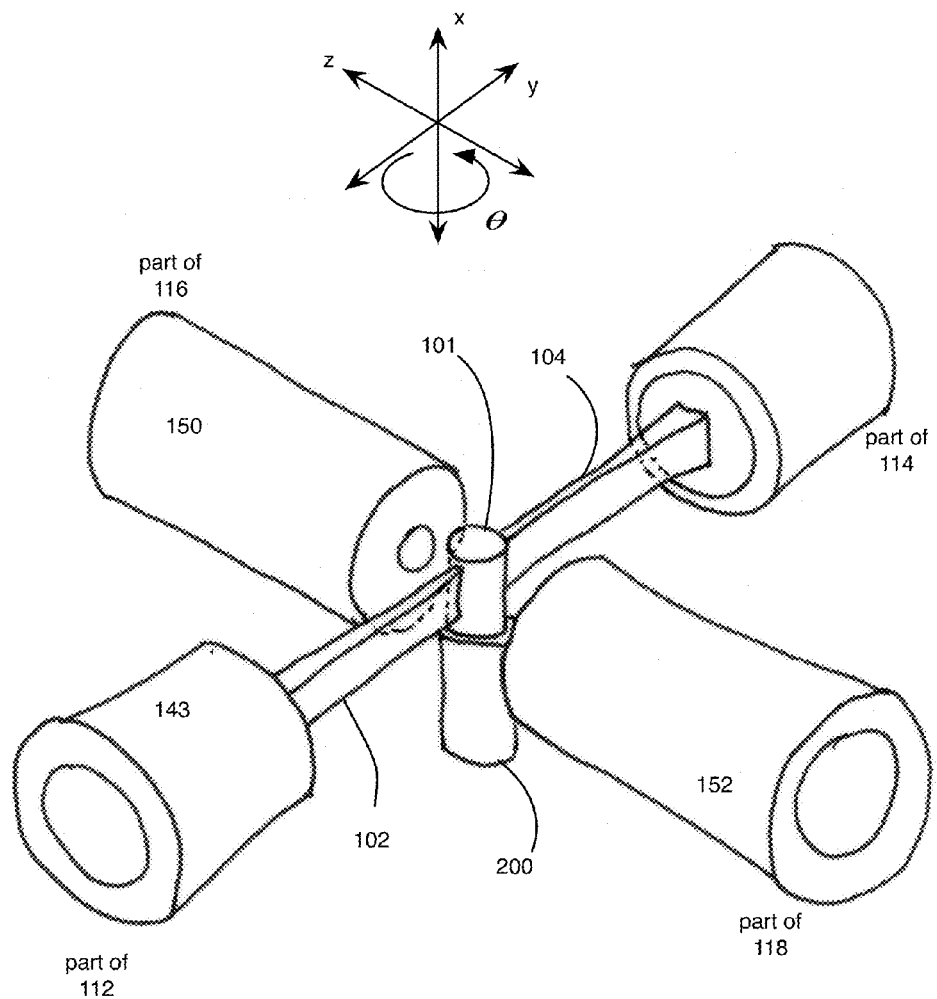
FIG. 4 is an expanded perspective view of a part of the exemplary microscope of FIG. 3 showing a specimen and objectives.

Next, exemplary detection subsystems 116, 118 will be discussed in greater detail. In some implementations, as shown in FIG. 3, both of the subsystems 116, 118 are designed with the same components. For example, the fluorescence light (or photons P) emitted from the specimen 101 is collected by opposing detection objectives 150, 152, and the collected light from respective objectives 150, 152 passes through a filter 154, 156, which rejects light of wavelengths outside a wavelength band centered around the wavelength of the fluorescence light to be detected. The filter 154, 156 can be mounted on a filter wheel (not shown) with other filters, so that the wavelength of rejected light could be changed by selecting a different filter on the wheel by merely rotating the wheel into a new position. The filters 154, 156 can be short-pass or band-pass filters, such as, for example, BrightLine fluorescence filters from Semrock, Inc, a part of IDEX Corporation of Lake Forest, Ill.

Light from the filter 154, 156 is directed through respective lenses 158, 160, which focus the light onto the sensor of the camera 106, 108. The lenses 158, 160 can be tube lenses.

In some implementations, the detection objectives 150, 152 can be high numerical aperture water-dipping objectives. For example, the objectives can be purchased from suppliers such as Carl Zeiss, Nikon, or Olympus. The detection objectives 150, 152 can be mounted or attached to scanners 162, 164, which are connected to and controlled by the connector blocks within the electronics controller 180. For example, the scanner can be a piezo-actuated scanner (a nanopositioner) such as the PIFOC® PI P-725 PIFOC long-travel objective scanner produced by Physik Instrumente (PI) GmbH & Co. KG of Germany.

The filter wheel can be purchased from Ludl Electronic Products Ltd. For example, the filter wheel can be the 96A354 6-slot filter wheel produced by Ludl. The filter wheels are operated by one or more servo controllers, which are connected to connector blocks within the electronics controller 180.

The tube lenses 158, 160 can be purchased from suppliers such as Carl Zeiss, Nikon, or Olympus, and the cameras 106, 108 can be scientific CMOS (complementary metal oxide semiconductor) image sensors (sCMOS sensors). The sCMOS sensors can be purchased from Andor Technology plc. or from PCO-TECH Inc. (formerly The Cooke Corporation). Or, the sCMOS sensors can be the Orca Flash 4.0 sCMOS sensor from Hamamatsu. The cameras 106, 108 are connected to full-configuration frame grabbers in the computational system 190 by a pair of standard data transfer cables, such as Camera Link® cables, that are a part of the electronics controller 180.

Specimen and Supporting Components

Next, a description of the specimen 101 and its associated optical, mechanical and electrical components is provided.

Figure 5A:
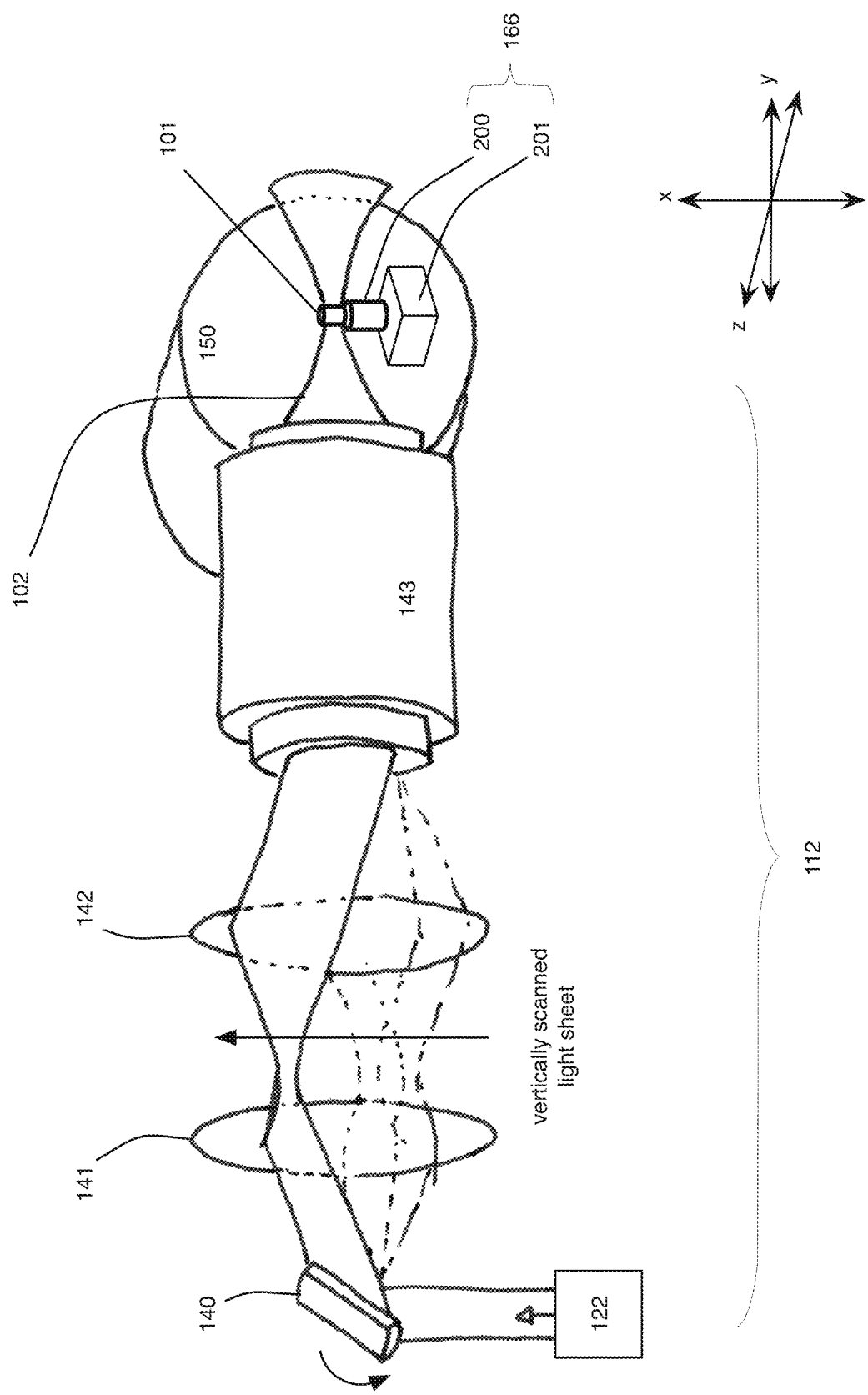
FIG. 5A is an expanded perspective view of an exemplary illumination system of the microscope of FIG. 3.
Figure 5B:
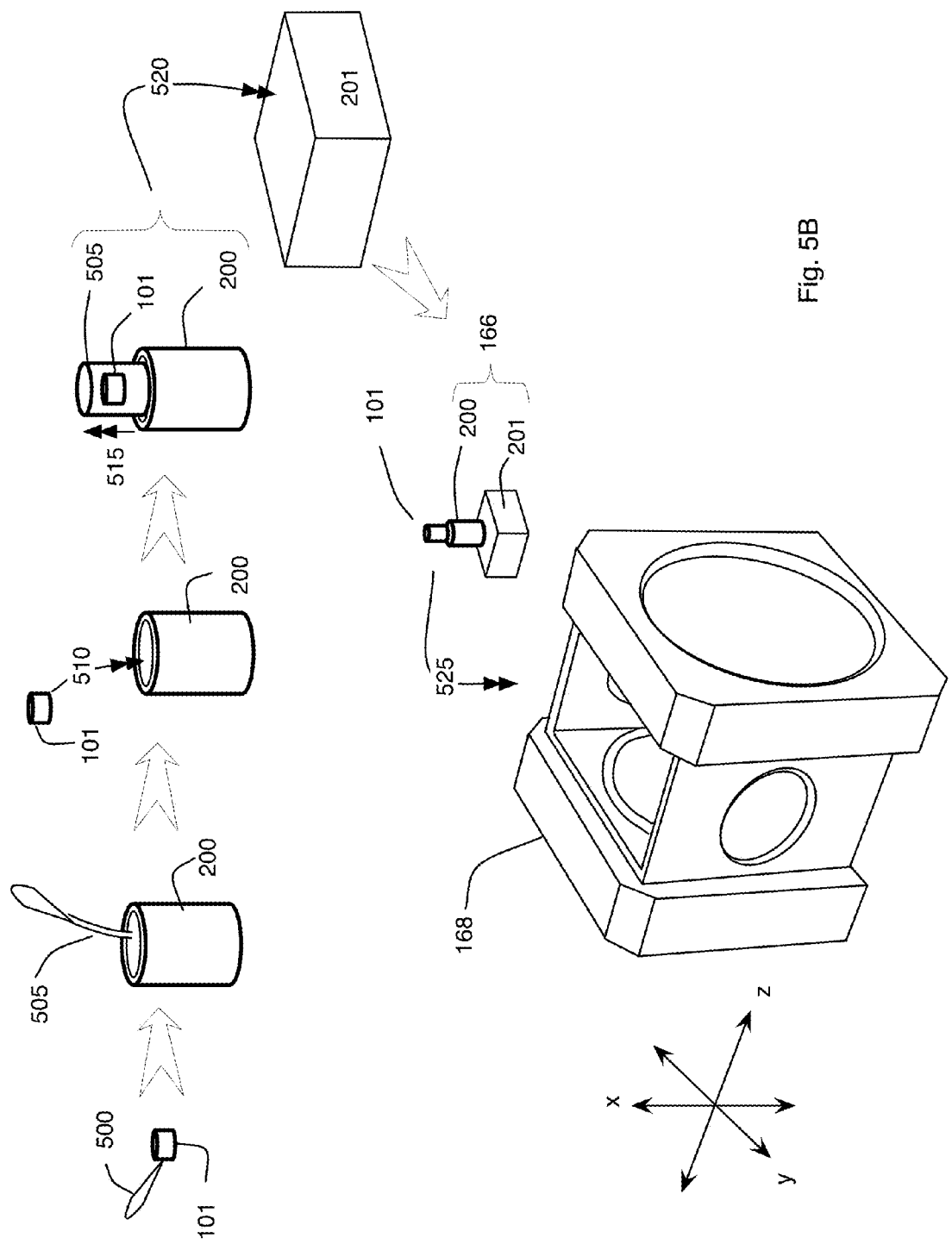
FIG. 5B is a perspective view showing exemplary steps for preparing the specimen and a chamber that holds the specimen in the microscope system of FIG. 3.

Referring also to FIGS. 5A and 5B, the specimen 101 is attached to a specimen holder 166 that enables the specimen 101 to be optically accessible to all of the illumination subsystems 112, 114 and the detection subsystems 116, 118. The specimen 101 and the holder 166 can be placed within a hollow space defined by a specimen chamber 168. For example, the holder 166 can include a glass capillary 200 that is mounted to a solid base 201. The base 201 of the specimen holder 166 can be produced from medical-grade stainless steel. The holder 166 can be a custom water-sealed flexible specimen holder.

The holder 166 is physically attached to a positioning system that provides a translation stage and a rotation stage, which is connected to the electronics controller 180. The translation stage can be set up to translate the holder 166 and thus the specimen 101 along three orthogonal directions, for example, along the x, y, and z axes. The rotation stage can be set up to rotate the holder 166 and thus the specimen about the x axes. The positioning system can be inside of or external to the specimen chamber 168.

One or more of the holder 166 and the chamber 168 can be connected to a thermoelectric cooling device such as an integrated Peltier cooler, heater, or thermoelectric heat pump to maintain the specimen 101 at a particular temperature.

The objectives in the illumination subsystems 112, 114 and the detection subsystems 116, 118 are directed at the center region of the chamber 168, at which the specimen 101 is positioned and located. In this implementation, the axis (which is the y axis) of the illumination subsystems 112, 114 is oriented perpendicularly to the axis (which is the z axis) of the detection subsystems 116, 118.

In some implementations, the positioning system for the holder 166 (and thus the specimen 101) can be a high performance stepper and servo motion control such as the NI PXI-7354 motion controller produced by National Instruments. This control can be connected to an interface within the electronics controller 180 such as a C-809.40 4-channel servo-amplifier/motion I/O interface produced by Physik Instrumente (PI) GmbH & Co. KG.

The chamber 168 has an internal hollow space having a volume that is large enough to accommodate the specimen 101 and the holder 166; for example, a chamber with full optical access from all sides to enable simultaneous light sheet illumination and fluorescence detection with four objectives. Full optical access and improved specimen positioning control (three-dimensional translation and one-dimensional rotation) can be realized by splitting the microscope sub-systems into two horizontal layers. For example, all optical systems could be located in an upper layer, whereas the specimen positioning system could be located underneath the specimen chamber 168 on a lower optical table. The specimen positioning system can be configured in an upright position (for example, along the x axis), thus permitting the use of exceptionally soft (0.4%) agarose gels for specimen embedding within the glass capillary 200 of the holder 166. Mechanical stability during imaging is largely provided by the solid base of the holder 166 on which the capillary is mounted.

The chamber 168 can be custom designed and built to provide enough views for the illumination and detection; in this example, four views. It can include a perfusion system. The specimen chamber 168 houses the specimen holder 166, and can also house a multi-stage adapter module for connecting the specimen holder 166 to the specimen positioning system and the custom perfusion system. Using the positioning system, the holder 166 can be translated in three dimensions and rotated around its main axis (the x axis) without breaking the water seal. The chamber 168 is open to two opposite sides to accommodate the water-dipping detection objectives and contains two windows with coverslips on the remaining two sides for laser light sheet illumination. The top of the chamber 168 is open for mechanical or optical access and allows background illumination with a cold light source. The chamber 168 has inlet and outlet valves connected to the perfusion system, which is operated by a dual-channel 12-roller pump (for example, a REGLO by Harvard Apparatus of Holliston, Mass.). The pump can be connected to the chamber 168 by a clear, flexible tubing having some level of resistance to chemicals, such as Tygon™ tubing, and the tubing is guided through a bench-top incubator (Model 107 bench-top environmental chamber, TestEquity) for temperature control and oxygenation of the specimen 101.

In some implementations, the specimen positioning system can be magnetically connected to the specimen holder 166 in the chamber 168.

As mentioned above, the chamber 168 can also include a custom perfusion system, which is a pump that enables the replacement of the buffer vapor in the cavity of the chamber 168 at a desired rate, to maintain physiological conditions for the specimen 101. Such a perfusion system can be beneficial for long-term imaging experiments with specimens 101 that can be difficult to culture, such as, for example, mouse embryos, or for imaging that requires stable environmental conditions, such as temperature, pH, oxygen concentration, sugars and amino acids in surrounding medium. The perfusion system can be used in combination with a temperature control system that is thermally connected to the chamber 168 to permit temperature regulation of the chamber and the environment around the specimen 101.

Electronics Controller

Figure 6:
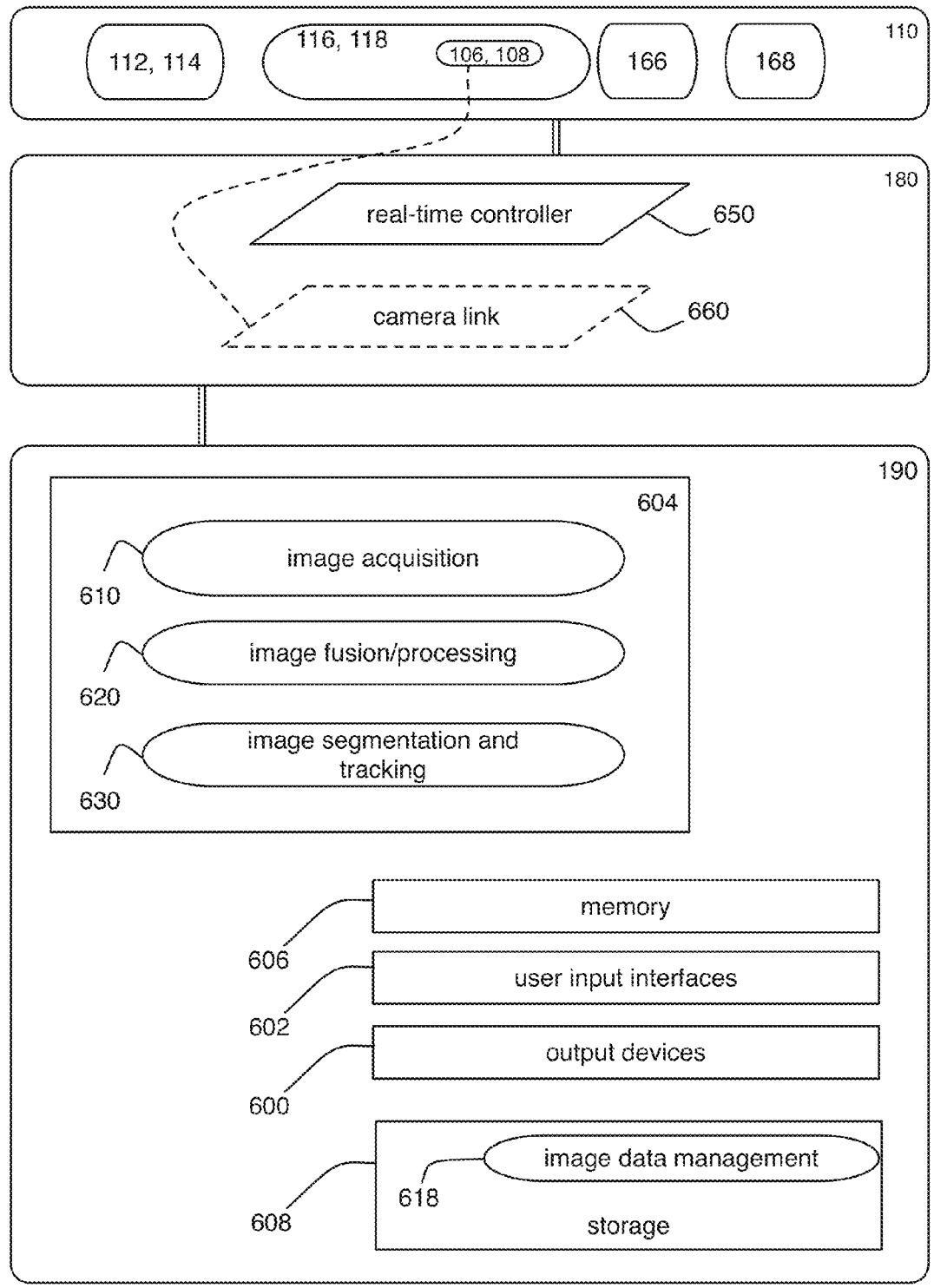
FIG. 6 is a block diagram showing details of an exemplary electronics controller and an exemplary computational controller of the microscope system of FIG. 1A.

Referring to FIG. 6, all optical and mechanical components (such as within the illumination subsystems 112, 114, the detection subsystems 116, 118, or the specimen holder 166 and specimen chamber 168) of the microscope 110 are operated and synchronized by a high-performance real-time electronics controller 650 provided within the electronics controller 180. The real-time controller 650 communicates with the computational system 190 to coordinate the simultaneous image acquisition workflow at a rate of 350 megabyte/second. The electronics controller 180 can also include special camera links 660 for connecting directly to the cameras 106, 108.

All of the optical, mechanical, and electrical components within the optical microscope 110 are connected to components within the controller 650 to provide real-time control in each of the "arms" of the microscope; with each arm being one of either the illumination subsystems 112, 114 or the detection subsystems 116, 118. The controller 650 also includes an automated alignment module for rapid relative positioning and orientation of the two light sheets 102, 104 and the respective focal planes. The controller 650 modifies the various optical, mechanical, and electrical components of the optical microscope to provide twenty degrees of freedom of motion to optimize the fluorescence signal.

In one general aspect, the real-time electronics controller 650 is a real-time controller such as a PXI-8110 2.2 GHz Quad Core embedded controller by National Instruments Corporation of Austin, Tex. This controller can run a LabVIEW Real-Time operating system, and is equipped with three I/O interface boards (such as the PXI-6733 high-speed analog output 8-channel board, also by National Instruments) linked to BNC connector blocks (such as the BNC-2110 shielded connector block, also by National Instruments) as well as a serial interface board (such as PXI-8432/2, also by National Instruments). The real-time controller 650 communicates with the computational system 190 by way of a high-speed data transmission such as Gigabit Ethernet.

In addition to the real-time controller 650, the electronics controller 180 can also include a motion controller and analog and digital input/output channels on separate controllers. The motion controller can be a PXI-7354 motion controller from National Instruments and it can include a plurality of I/O controllers such as the PXI-6733 controllers from National Instruments, having eight analog outputs and eight digital I/O channels each.

All time-critical tasks can be performed within the electronics controller 180, with the remaining tasks (such as collecting and visualizing frames recorded by the cameras 106, 108) being assigned to the computational system 190.

Computational System

Referring again to FIG. 6, the computational system 190 can include a computer such as a workstation that has the ability to store, retrieve, and process data. Thus, the computer includes hardware such as one or more output devices 600 such as a monitor or a printer; one or more user input interfaces 602 such as a keyboard, a mouse, a touch display, or a microphone; one or more processing units 604, including specialized workstations for performing specific tasks; memory (such as, for example, random-access memory or read-only memory or virtual memory) 606; and one or more storage devices 608 such as hard disk drives, solid state drives, or optical disks. The processing units can be stand alone processors, or can be sub-computers such as workstations in their own right.

The specialized workstations include an on board processing unit, in addition to memory, and software for running specific tasks. The specialized workstations includes an image acquisition workstation 610, an image processing workstation 620, and an optional image segmentation and tracking workstation 630.

The storage devices 608 include, among others, an image data management storage unit 618 that receives information from the image acquisition workstation 610 and also is equipped to receive its own processors, for additional processing capabilities.

The workstations include their own software modules, which include a set of instructions that tells the hardware within the electronics controller 180 what to do.

The computational system 190 is designed for high-speed imaging experiments with up to several days of continuous image acquisition. The computational system 190 is capable of recording more than one million high-resolution images in uninterrupted high-speed imaging sessions with a total data set size of up to ten terabytes per specimen. In order to permit high-speed recording, each of the lines connecting the image acquisition workstation 610 to the image data management unit 618 and to the controller 650 can be set up as a glass fiber network pipeline, providing 10 gigabit/second data speed thus allowing recording up to ten million high-resolution images or 100 terabytes per specimen 101 for long-term imaging sessions. A maximum recording capacity of one petabyte can be realized if the image data management unit 618 uses a three-dimensional wavelet compression technique having an average ratio of 10:1.

The image acquisition workstation 610 and the multiview image processing workstation 620 are developed for content-based image registration and multiview image fusion, respectively, which efficiently incorporates prior knowledge of the optical implementation to process raw image data at a rate of about 200 megabyte/seconds. The image acquisition workstation 610 is capable of real-time image registration and integrates with the image processing workstation 620 for large-scale data management. Since the computational system 190 acquires multiple views simultaneously, fast and accurate image registration (alignment of images) within the image acquisition workstation 610 is achieved without the need of fiducial markers in the imaging volume IV.

In one implementation, the computational system 190 is a Windows-based personal computer having twelve physical core processors within the processing units 604 operating at 3.3 GHz and accessing 64 gigabytes (GB) of RAM in memory 606. The processing unit 604 can run a LabVIEW® Developer Suite. The memory 606 can also contain a fast RAID system of hard disk drives having a total capacity of 2×5 TB (22 hard disks with 600 GB capacity each, combined in two RAID-6 arrays with two disk redundancy each) and 2 NI PCIe-1429 full-configuration frame grabbers. Having two virtual disk drives allows assigning one drive to each camera 106, 108 or writing images in an alternating manner on both drives using only a single camera 106, 108. Typically, however, both cameras 106, 108 are used in an experiment.

In the following, we provide a short description of the workflow in the computational system 190, referring to the z axis as the optical axis of the detection subsystems 116, 118, the y axis as the optical axis of the illumination subsystems 112, 114, and the x axis as the remaining axis to form a Cartesian coordinate system.

In general, the image acquisition workstation 610 performs a registration of images, which is a process that aligns the images from the cameras 106, 108. In general, the image processing workstation 620 performs a fusion of the images, which is a process of combining the registered images into a single representation or image. In particular, images are fused by combining the information content of the images into a single image. Details about fusion are discussed below.

The image data management unit 618 provides a high-throughput image storage pipeline for sustained data streaming at 600 megabytes/second; uninterrupted long-term image acquisition of 100 terabyte sized data sets, and a wavelet-based lossless image compression (for example, ten-fold).

In some implementations, the image acquisition workstation 610 includes a pair of 6-core central processing units (CPUs), one for each of the cameras 106, 108, for processing the images. The CPUs can be, for example, Xeon® Processors X5680 purchased from Intel Corporation of Santa Clara, Calif. The image acquisition workstation 610 can also include dedicated memory such as RAM (for example, 144 GB DDR-3 RAM from Kingston) for image ring buffers and online processing, a 24-channel RAID controller (for example, model 52445 from Adaptec) with 22 SAS-2 hard disks (for example, the Cheetah 15K.7 by Seagate) combined in a RAID-6 for high-speed image acquisition, a 10 Gigabit fiber network adapter (such as, for example, EXPX9501AFXSR, Intel Corporation) for online data streaming, a graphics adapter (such as, for example, GeForce GTX470, Nvidia Corporation) for GPU-based processing, two Camera Link frame grabbers (such as, for example, Neon, BitFlow; or PCIe-1429, National Instruments) and a server board (such as, for example, X8DAH+-F, Supermicro).

The image acquisition workstation 610 relays the raw multiview data stream to the image processing workstation 620 and the image data management unit 618 by way of optical fibers. The software used in the workstation 610 can be written in, for example, Matlab and C++ for providing high-throughput multiview image processing and real-time image data management.

In some implementations, the image processing workstation 620 includes a pair of 6-core CPUs (such as, for example, Xeon® Processors X5680 purchased from Intel Corporation of Santa Clara, Calif.), 96 GB DDR-3 RAM (Kingston), a 16-channel RAID controller (51645, Adaptec) with 2 SAS-2 hard disks (AL11SE 147 GB, Toshiba) combined in a RAID-1 for the operating system and 10 SAS-2 hard disks (AL 11 SE 600 GB, Toshiba) combined in a RAID-6 for image data buffering, a 10 Gigabit fiber network adapter (EXPX9501AFXSR, Intel Corporation) for online data streaming, a high-performance graphics adapter (Quadro FX5800, Nvidia Corporation) for GPU-based processing, and a server board (S5520SC, Intel Corporation).

As mentioned above, the image data management unit 618 is connected to the image acquisition workstation 610 and the image processing workstation 620 by Gigabit optical fiber and includes a rack-mount server with triple-channel SAS interface and a 10 Gigabit fiber network adapter (EXPX9501AFXSR, Intel Corporation), as well as two 24-disk RAID enclosures (ESDS A24S-G2130, Infortrend). The RAID enclosures are equipped with 48 SATA-2 hard disks (Ultrastar A7K2000, Hitachi), which form two RAID-6 arrays for long-term imaging experiments and post-acquisition wavelet-compressed data storage.

Procedure

Figure 7:
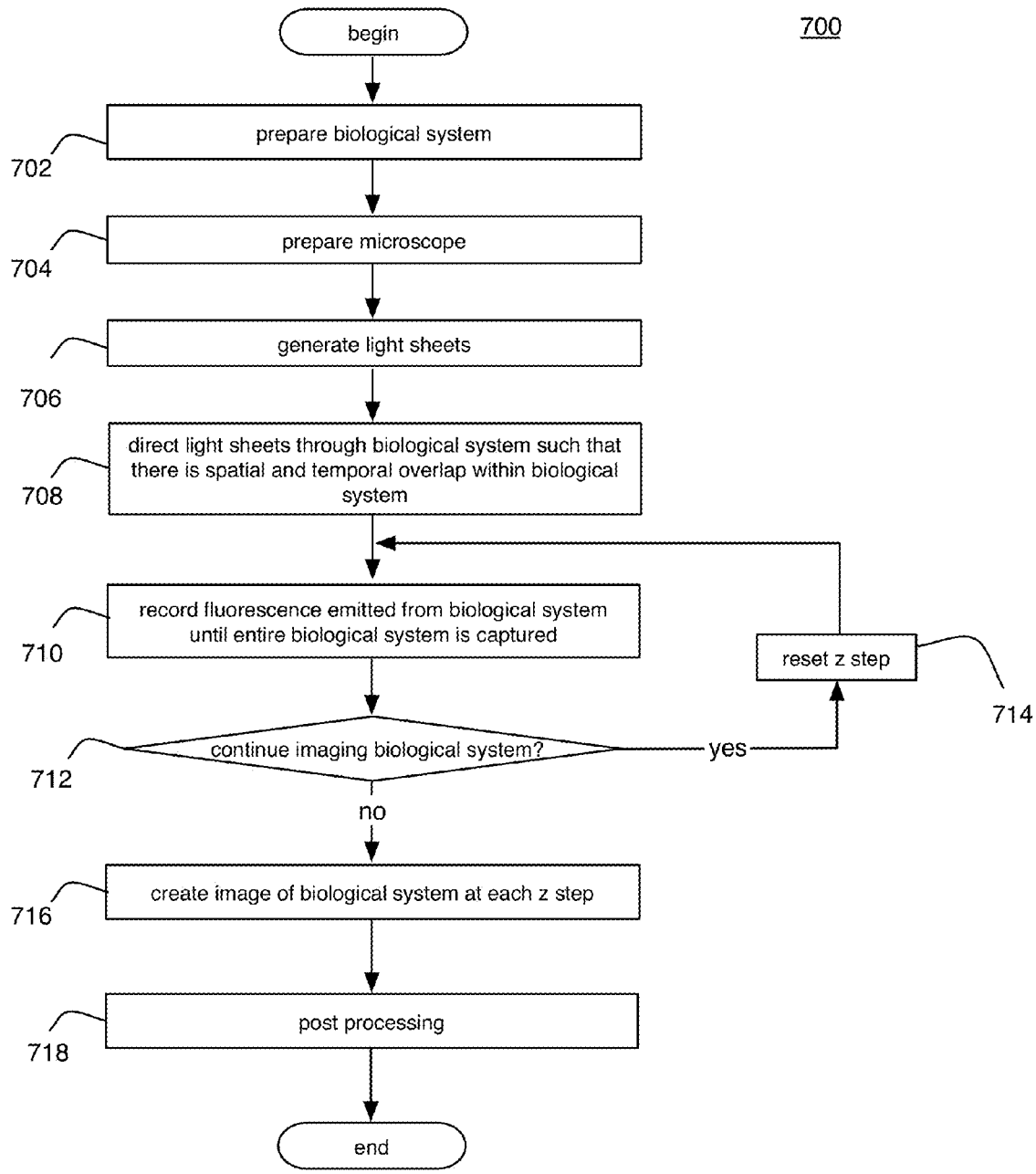
FIG. 7 is a flow chart of an exemplary procedure performed by the microscope system of FIG. 1A.

Referring to FIG. 7, a procedure 700 is performed by the microscope system 100 to image the complex biological specimen 101. Initially, the biological specimen 101 is prepared (702). The biological specimen 101 is prepared (702) by chemically and biologically preparing the specimen, physically transferring or mounting the specimen to the holder 166, and placing the holder 166 inside the chamber 168.

The microscope 110 is prepared (704), for example, by adjusting properties (such as the alignment) of the light sheets 102, 104. Once the microscope 110 is prepared, the light sheets 102, 104 are generated (706). The lights sheets 102, 104 are directed through the biological specimen 101 such that there is spatial and temporal overlap within the specimen 101 (708). The beginning of the illumination and recording of the fluorescence can start at the moment the fertilized egg is formed, to enable imaging of the biological specimen 101 in its development from a fertilized egg to a complex system.

Fluorescence emitted from the biological specimen 101 is recorded by the cameras 106, 108 until the entire biological specimen 101 is captured (710). It is then determined if the imaging of the biological specimen 101 should continue (712). For example, imaging can usually continue until the onset of strong muscle contractions in the developing embryo; at that point, imaging can be stopped because the specimen 101 becomes more physically active and can be more difficult to image. However, it is possible that imaging could continue past this developmental point.

If imaging is to continue (712), then the relative alignment between the light sheets and the biological specimen 101 is reset (714) and the fluorescence is once again recorded (710). The image of the biological specimen 101 is created (716) and additional post processing can be performed (718).

Next, a discussion of the preparation of the biological specimen 101 (702) is provided with reference to FIG. 5B. As an example, the specimen 101 can be microinjected 500 with some material such as drugs, labeled proteins (such as the fluorophores), or antibodies, as needed, and it could also be dechorionated (that is, the chorion (or outermost membrane) can be cleared or removed to enable subsequent imaging). If the holder 166 includes a glass capillary 200, then the capillary 200 can be pre-filled with a liquid 505 such as agarose gel, and then the specimen 101 can be carefully transferred 510 into the capillary 200.

After transferring into the capillary 200, the specimen 101 can be centered and properly oriented within the agarose gel 505 that is within the capillary 200 so that one of its axes (such as its anterior-posterior axis) is oriented parallel to the symmetry axis of the capillary 200. Moreover, during this step, the specimen 101 can be maintained at a stable temperature. After the gel is allowed to settle, the section of the gel 505 that contains the specimen 101 can be forced out 515 of the capillary 200 to provide full optical access to the specimen 101, as shown in the illustration of FIGS. 5A and 5B. The capillary 200 with the specimen 101 embedded within the gel 505 can then be mounted 520 to the base 201 so that its symmetry axis aligns with the x axis of the microscope 110. And, the base 201 with the capillary 200 and specimen 101 embedded within the gel 505 is mounted 525 within the chamber 168.

The microscope can be prepared 704 by adjusting one or more of the following aspects of the microscope 110. For example, the displacement of each light sheet 102, 104 away from the y axis that passes through the mounted biological specimen 101 can be adjusted. The tilt of each light sheet 102, 104 relative to the y axis that passes through the mounted biological specimen 101 can be adjusted. The relative intensity of the light sheets 102, 104 can be adjusted. One or more of the tilt and the displacement of each of the detection subsystems 116, 118 relative to the z axis that passes through the mounted biological specimen 101 can be adjusted. The relative detection efficiency of each of the detection subsystems 116, 118 can be adjusted.

The light sheets 102, 104 are generated (706) by rapid laser scanning using the optical scanner devices 140. The light sheets 102, 104 can be generated from a continuous wave light sheet, which is shuttered so that each light sheet arrives at a distinct point in time in the biological specimen 101 but still within the temporal overlap. The light sheets 102, 104 can be generated from pulsed wave light sheets, and can be activated in synchrony.

For an implementation that uses one-photon excitation, the activation of the light sheets 102, 104 can be alternated in the two illumination subsystems 112, 114 for each z plane that is being imaged at any moment. For example, fast laser shutters can be used in both of the illumination subsystems 112, 114 to stagger the light sheets 102, 104 when using continuous illumination with one-photon excitation.

For an implementation that uses two-photon excitation, the light scattering in the illumination process is minimal, and fluorescence excitation is spatially confined to the image volume IV so that there is little degradation in image quality in the biological specimen 101 outside of the central region 103, and thus, the illumination subsystems 112, 114 can be activated in synchrony. Moreover, it is possible to slightly displace the two focal volumes of the respective light sheets 102, 104 just enough to obtain a continuous image without significant overlap of the fluorescence contribution from each light sheet 102, 104. In contrast to one-photon excitation, there is no blurring of the fluorescence signal contribution along the illumination path, since the two-photon excitation is effectively suppressed once the light sheet becomes too wide.

For one-photon excitation, a laser operating at 488 nm can be set to a power of a few hundred µW in the live imaging of *Drosophila* embryos. This corresponds to an exposure of the specimen to about 7-10 µJ light energy per acquired image pair, or about 1-3 mJ for the acquisition of all images in a four-view image data set of the entire specimen per recorded time point. For two-photon excitation, a laser power of about 300 mW can be used to perform live imaging of *Drosophila* embryos at an excitation wavelength of 940 nm.

Figure 8A:
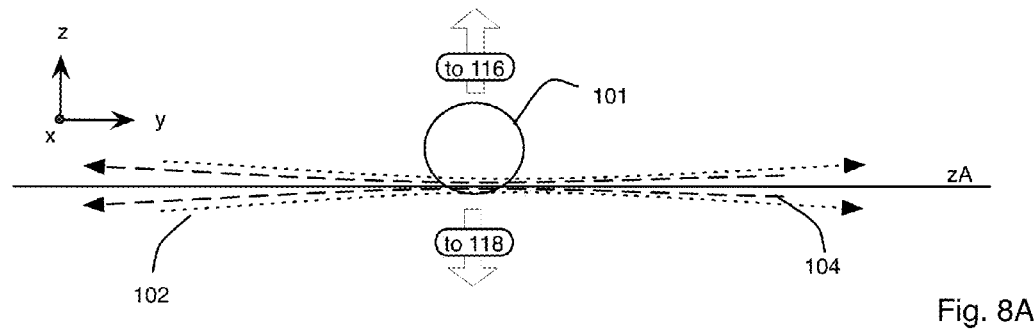
FIGS. 8A-8D are block diagrams showing an exemplary imaging scheme in which the relative position of the specimen and the light sheets is modified along a detection axis within the microscope system of FIG. 1A.

The light sheets 102, 104 are directed through the biological specimen 101 such that there is spatial and temporal overlap within the specimen 101, as shown schematically in FIG. 1B. Initially, the light sheets 102, 104 can be directed along a base x-y image plane (located at zA) as shown in FIG. 8A.

The fluorescence emitted from the biological specimen 101 is detected by the cameras 106, 108 as images, and this image data is received by and properly processed by the electronics controller 180, and then recorded within the computational system 190 (710).

The fluorescence at each x-y image plane of the specimen 101 is recorded until the entire specimen 101 is captured (710). For example, after the fluorescence at the zA image plane is recorded (see FIG. 8A), the relative placement along the z axis between the biological specimen 101 and the light sheets 102, 104 is modified by a step along the z axis so that the next x-y image plane can be recorded. In this way, the fluorescence emitted from the biological specimen 101 is recorded incrementally at each of the x-y image planes of the biological specimen 101.

Figure 8B:
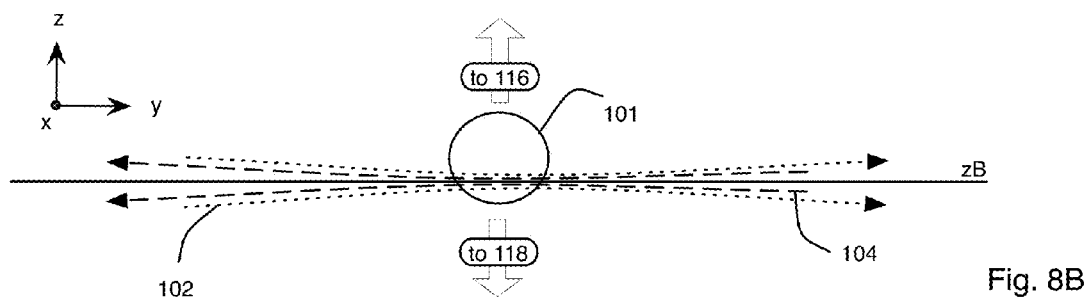
Figure 8C:
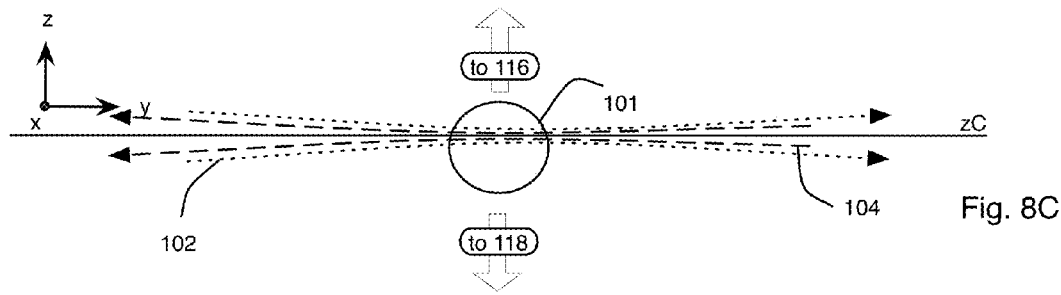
Figure 8D:
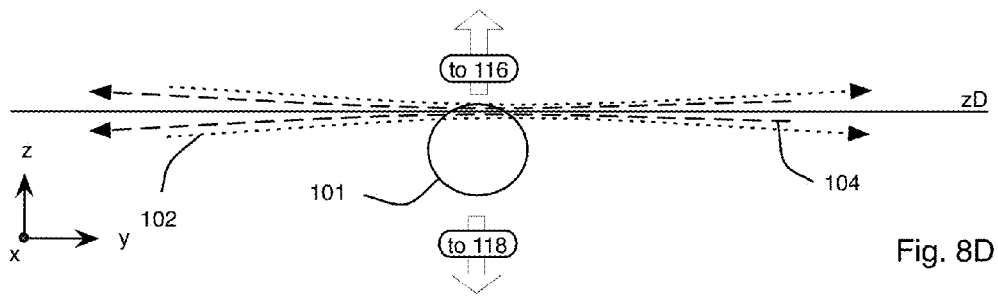

For example, in FIG. 8B, the fluorescence is recorded at the x-y image plane located at zB; in FIG. 8C, the fluorescence emitted from the biological specimen 101 is recorded at the x-y image plane located at zC; and in FIG. 8D, the fluorescence emitted from the biological specimen 101 is recorded at the x-y image plane located at zD.

In some implementations, the relative placement between the biological specimen 101 and the light sheets 102, 104 can be modified by moving the biological specimen 101 along the z axis in steps while maintaining the light sheet 102, 104 and the detection subsystems 116, 118 stationary. One advantage of this method is that it is possible to record larger imaging volumes since the linear motors that move the biological specimen 101 have a longer travel range than the actuators that control the light sheet 102, 104, and the detection subsystems 116, 118.

In other implementations, the relative placement between the biological specimen 101 and the light sheets 102, 104 can be modified by moving the light sheets 102, 104 and the detection subsystems 116, 118 in synchrony along the z axis in steps while maintaining the biological specimen 101 stationary. One advantage of this faster imaging method is that it can be faster to image because the actuators that control the light sheets 102, 104 and detection subsystems 116, 118 are much faster than the linear motors actuating the biological specimen 101. Another advantage of this imaging method is that the position of the light sheets 102, 104 can be adjusted as it is moved to also provide optimal or improved image quality at each step along the z axis and thus can provide an improvement in image quality across the specimen 101.

In some implementations in which the cameras 106, 108 are scientific CMOS (sCMOS), in order to acquire one image, the exposure time for the camera 106, 108 can be set to 0.1-10 milliseconds (ms). In this case, because of the specific properties of the trigger mode for the sCMOS camera, typical image acquisition times have a range of about 10-30 ms, including the time for scanning the light sheets 102, 104 and transferring the data of the images to the computational system 190 for processing.

In some implementations, both of the cameras 106, 108 are synchronized, that is, two images are recorded simultaneously within the acquisition time range. Thus, for the sCMOS cameras, it is possible to record at a rate of about 2×100 images per second, with an image size of 2048×2048 pixels, that is, 4 Megapixels.

Using the faster imaging method described above, it is possible to record the entire three dimensional data set of a biological specimen 101 having a thickness of about 200 µm (along the z axis) within a time frame of 1-3 seconds (710).

In some implementations, the computational system 190 creates an image of the biological specimen 101 (716) after the data acquisition of the images of the entire biological specimen 101 has completed. As discussed above, in some implementations, the data acquisition of the images can be completed at the onset of strong muscle contractions in the embryo. However, it is possible to stop data acquisition earlier or later than this point in development, depending on what needs to be imaged.

In other implementations, the computational system 190 processes the data during the acquisition of the data by the microscope 110. For example, it is possible that the computational system 190 could be set up to process all data recorded after the fluorescence from the entire biological specimen 101 is captured at a particular x-y image plane (710) so that the computational system 190 is processing the data while the microscope 110 continues to record the fluorescence at the next x-y image plane. Other setups for multitasking the creation of the image with the recordation of the fluorescence are possible.

For simplicity, the following discussion assumes that in step 716, the imaging has completed and all data has been collected to create the image of the biological specimen 101.

Figure 9:
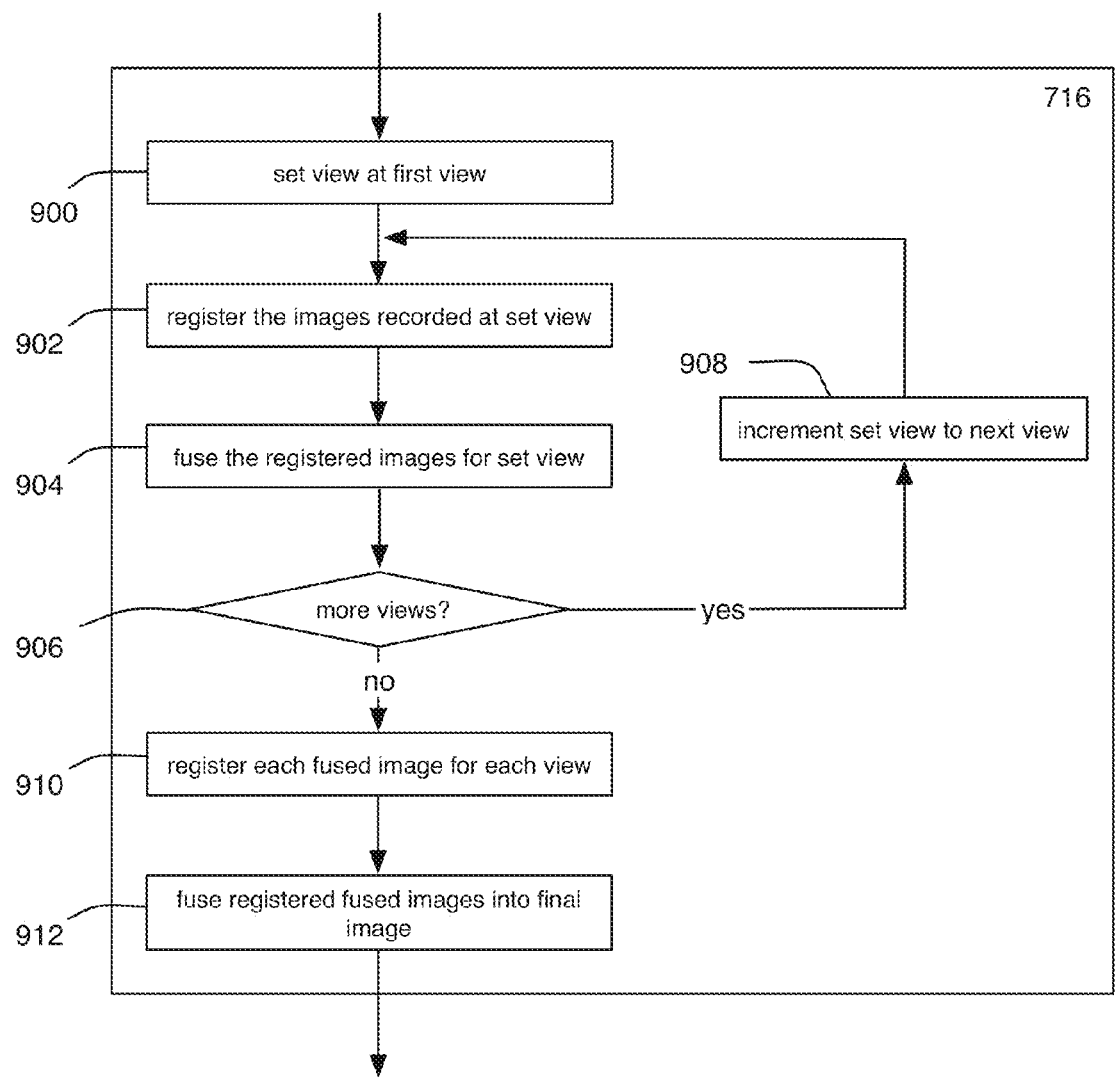
FIG. 9 is a flow chart of an exemplary procedure for creating an image of the specimen as performed by the microscope system of FIG. 1A.

Referring also to FIG. 9, the microscope system 100 performs an exemplary procedure 716 for creating an image of the biological specimen 101 at each of the x-y image planes that were acquired and recorded (710). For example, an image of the biological specimen 101 is created at each of the x-y image planes corresponding to the exemplary values of zA, zB, zC, and ZD shown, respectively, in FIGS. 8A-D.

Figure 10A:
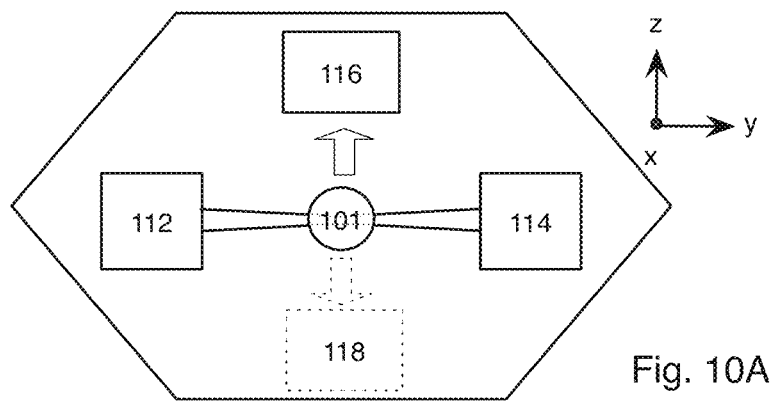
FIGS. 10A-10C are block diagrams of the microscope within the microscope system of FIG. 1A showing exemplary steps performed during the procedure of FIG. 9.

Initially, one of the detection subsystems is set as the first view to be imaged (900). For example, the detection subsystem 116 (as shown in FIG. 10A) can be set as the first view to be imaged.

Images of the biological specimen 101 that were recorded at this set view (the detection subsystem 116) are registered (902). This means that the images that are captured or recorded by the detection subsystem 116 and stored within the computational system 190 are aligned with each other. In particular, the image obtained from the illumination of the biological specimen 101 with the light sheet 102 is aligned with the image obtained from the illumination of the biological specimen 101 with the light sheet 104.

In some implementation, registration at the set view can involve the following procedure. Specifically, the image acquisition workstation 610 performs data interpolation and calculates three-dimensional masks that envelope the recorded image of the biological specimen 101 obtained from the illumination with the light sheet 102 and the recorded image of the biological specimen 101 obtained from the illumination with the light sheet 104. A Gaussian filter can be used for envelope smoothening. Using the combined masks, the geometrical center of the biological specimen 101 along the axis of the incident light sheets (the y axis) is calculated as a function of the location in the x, z plane. The resulting two-dimensional coordinate matrix indicates the y-centers of the optical illumination light path as a function of the location in the x, z plane in a first-order approximation. Using this matrix, slices of about 10 pixel thickness are extracted, background-corrected and registered for both images. The optimal transformation settings are determined, considering sub-pixel-precision z-translation and y-rotation as the only degrees of freedom.

The choice of a data slice in the center of the optical light path for the purpose of this first registration step is useful for those biological specimens 101 having bilateral optical symmetry with respect to the x, z plane (such as *Drosophila* and zebrafish embryos) and a generally reasonable starting point in the absence of detailed knowledge of the three-dimensional optical properties of the biological specimen 101. The coordinate system of the recorded image obtained from illumination with the light sheet 102 can constitute a reference or first channel; and the data of the image obtained from illumination with the light sheet 104 (the second channel) can be transformed into the coordinate system of the reference channel by global application of the transformation parameters determined for the registration slice.

The image processing workstation 620 subsequently determines average intensities in the registration slices and applies the corresponding intensity correction factor to the second channel.

Next, the registered images at the set view are fused (904) to form a fused image at this set view; which means that the information content of the registered images are combined into a single representation of an image. For example, if different parts or structures of a large object are captured in the different registered images and these images complement each other with respect to their information content, then the fusion of the images generates a single fused image that shows all of these parts or structures at the same time, and at the resolution or at the level of detail present in the contributing individual images.

In some implementation, fusion of the registered images at the set view can involve the following procedure. The image processing workstation 620 fuses the two data sets by one of the following three methods: global 5-level wavelet decomposition with a Daubechies D4 basis (for maximum quality), linear blending in a 20-pixel transition region relative to the coordinates of the registration matrix (for large convex specimens with complex optical properties), or global arithmetic averaging (for maximum speed).

Figure 10B:
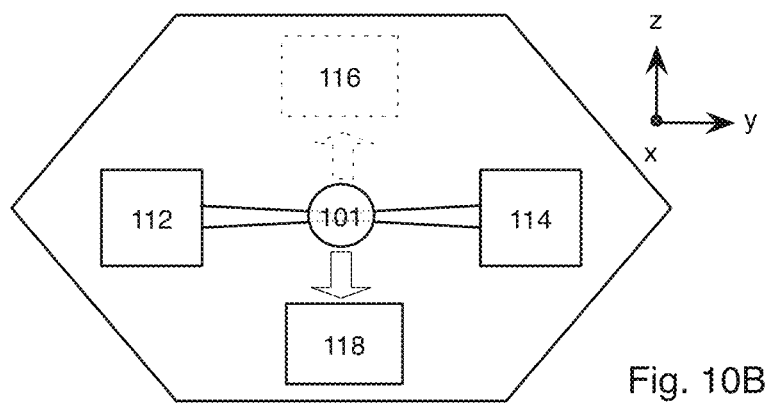

Next, it is determined whether there are any other views of the biological specimen 101 that were imaged (906) and if there are, then another detection subsystem is set as the view to be imaged (908). For example, the detection subsystem 118 (as shown in FIG. 10B) can be set at step 908 as the view to be imaged next.

Images of the biological specimen 101 that were recorded at this set view (the detection subsystem 118) are registered (902); and these registered images at this set view are then fused (904) to form a fused image at this set view, as discussed above.

Figure 10C:
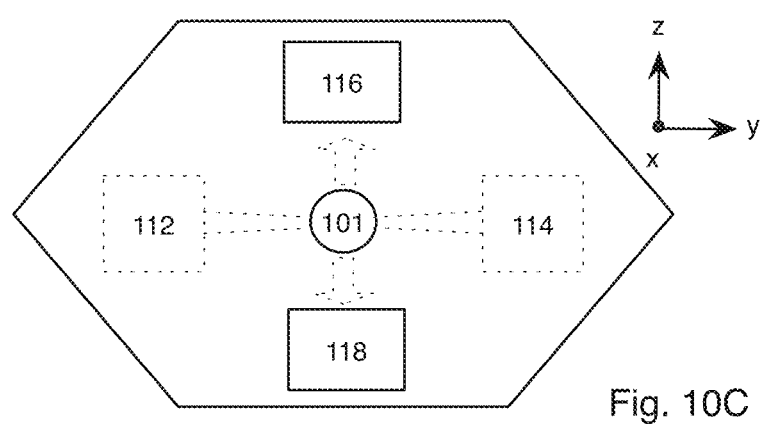

If it is determined that there are no other views taken of the biological specimen 101 that were imaged (906), then the computational system 190 registers the fused images (or fused data sets) that were formed at each view (910). Thus, in the example above in which there are only two views, the fused image obtained from the data taken by the detection subsystem 116 is aligned with the fused image obtained from the data taken by the detection subsystem 118, as shown in FIG. 10C.

For example, the image acquisition workstation 610 calculates the three-dimensional masks that envelope the recorded biological specimen 101 in the two fused data sets, using a Gaussian filter for envelope smoothening. Using the combined masks, the geometrical center of the specimen 101 along the axis of the detection sub-systems (z-axis) is calculated as a function of (x, y) location. The resulting two-dimensional coordinate matrix indicates the z-centers of the optical detection light path as a function of (x, y)-location in a first-order approximation. This coordinate matrix is then used to extract slices of 10 pixel thickness from the fusion data sets. The optimal transformation settings for registration of these two slices are determined, considering sub-pixel-precision x- and y-translations as well as z-rotation as degrees of freedom.

A region in the center of the optical detection light path can be used for the purpose of the second registration step, since the two detection subsystems 116, 118 typically provide comparable image quality in this location. The fused data set for the subsystem 116 constitutes the reference data set. The fused data set for the subsystem 118 is transformed into the coordinate system of the reference data set by global application of the transformation parameters determined for the registration slice.

Next, the computational system 190 fuses these now aligned (registered) fused data sets into a final image representative of the image x-y plane of the biological specimen 101 that corresponds to the spatial and temporal overlap of the light sheets 102, 104 within the specimen 101 (912).

As an example, image processing workstation 620 operates on the aligned (registered) fused data sets for the two detection subsystems 116, 118, in direct analogy to the procedure described above for the fusing the registered images at each of the subsystems 116, 118.

Figure 11:
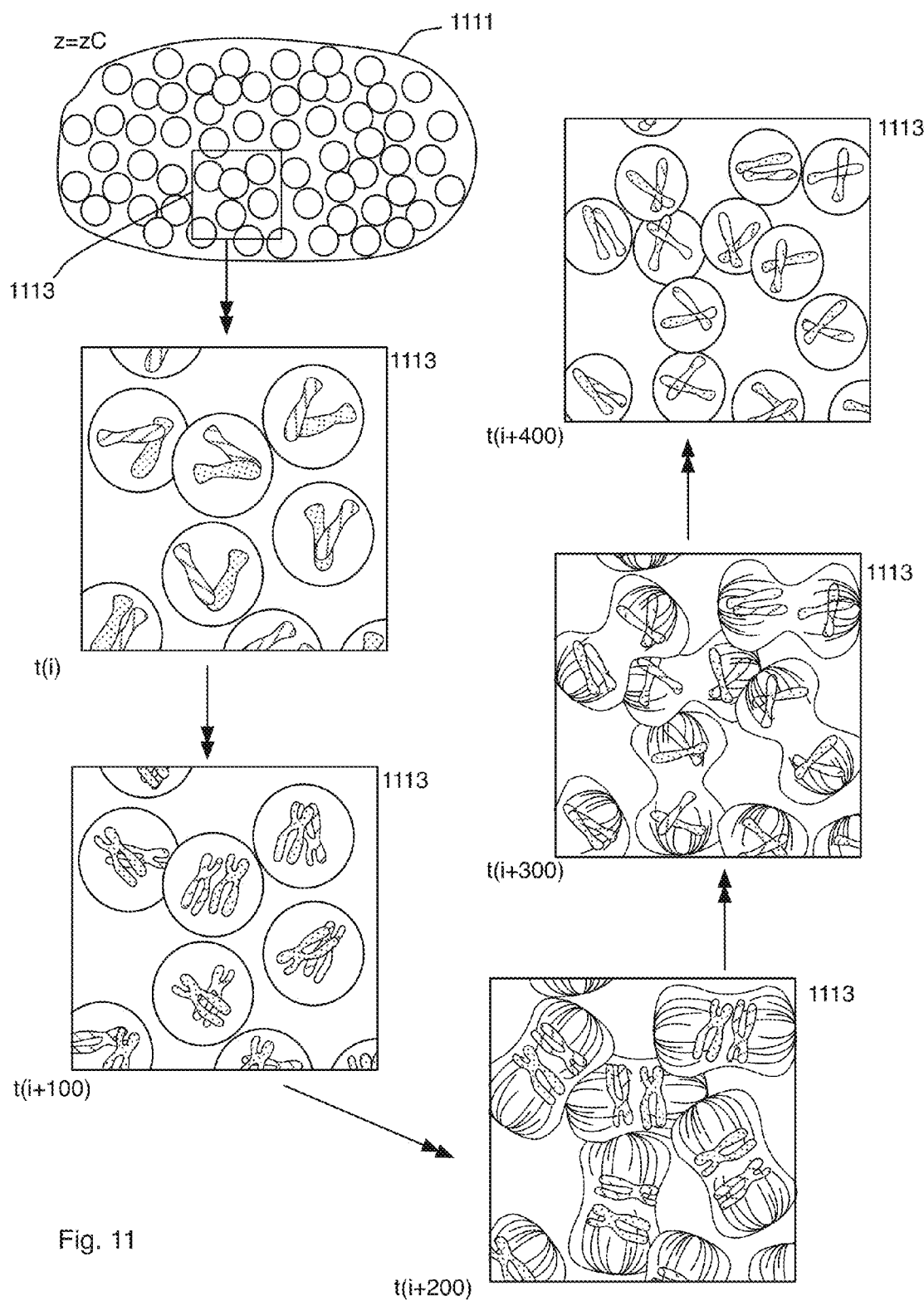
FIG. 11 is a diagram of a schematic representation of a specimen showing the development of the specimen at exemplary points in time as the image is captured using the microscope system of FIG. 1A.

For example, as shown in FIG. 11, for fluorescence emitted from the biological specimen 101 and recorded at the x-y image plane located at z equaling zC (as shown in FIG. 8C), a final image 1111 is created for the slice through the biological specimen 101 at the value of z=zC. The image of the biological specimen 101 is created for each x-y image plane that is imaged along the z steps. It is possible to create a maximum-intensity projection of all of these images to form a three dimensional image of the biological specimen 101.

As also shown in FIG. 11, a time series is taken at specific intervals of time (t(i), t(i+100), t(i+200), t(i+300), t(i+400)), measured in arbitrary units, for the sub-region 1113 of the recorded image 1111. This time series shows the nuclear dynamics during one mitotic cycle (such as the $13^{th}$ mitotic cycle) of the specimen 101. The microscope system 100 is able to produce images like this that quantitatively resolve the chromosomes within the cell nucleus across the entire biological specimen 101. In this example, exemplary intervals of time are shown, but many more intervals of time can be captured, as discussed in the examples below.

In summary, the procedure 700 provides for simultaneous four-view imaging data. It employs multi-threading to take full advantage of the computational infrastructure within the computational system 190, and achieves an image data processing rate of 200 megabytes per second when operating in full-processing mode and a four times higher rate when using interpolated transformation parameters.

Computation of these transformation parameters and image fusion can be performed by the workstations within the computational system 190 and can be coded in any suitable programming language, such as, for example, Matlab and/or C++. This conceptual separation allows considering only the degrees of freedom relevant for the particular data type in the respective module and, thus, performing the multiview fusion more efficiently.

As discussed above, post processing can be performed (718). Post processing can involve steps carried out by the computational system 190 or can involve steps carried out by the operator.

Figure 12A:
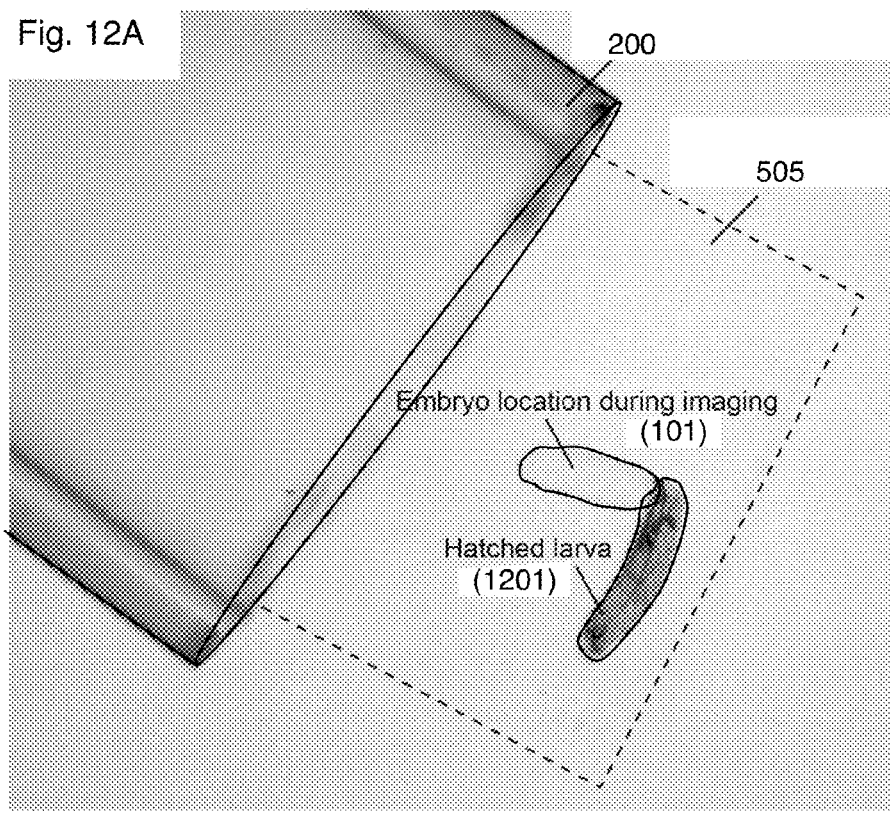
FIGS. 12A and 12B are images of the specimen taken during a post processing step in the procedure of FIG. 7.
Figure 12B:
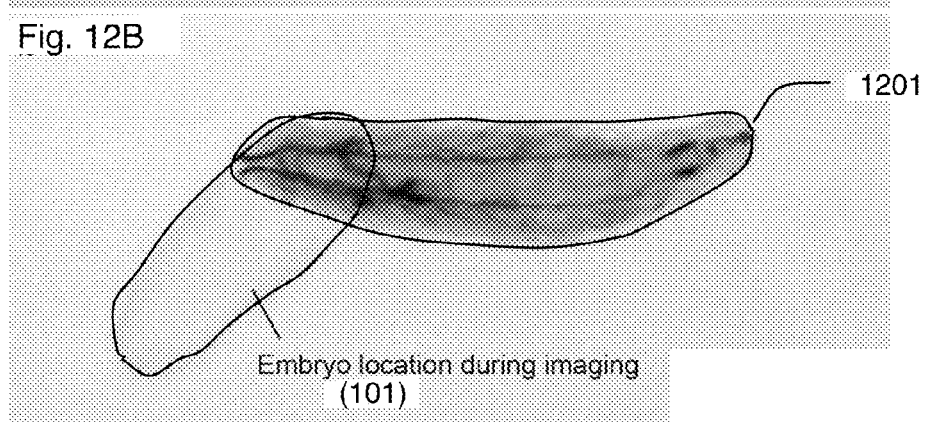

For example, with reference to FIGS. 12A and 12B, the biological specimen 101, which can be embedded in the agarose gel 505, can be transferred to a dissection microscope to control for normal hatching of larvae 1201. The biological specimen 101 (which is now the larvae 1201) could be monitored to verify physiological development.

As another example, the computational system 190 could create a single image from the "stack" of two-dimensional images that are created; in which the stack of images corresponds to each image created for each z step at step 912. The single image can be created by projecting the maximum pixel intensity levels through the entire stack onto a single plane. This single image can be considered to be a two dimensional visualization of the three-dimensional data that is recorded with the microscope system 100 and it can provide an overview of the recording.

EXAMPLES

Multiview Imaging of *Drosophila* Embryos

The microscope system 100 was used for performing simultaneous multiview imaging of developing *Drosophila* embryos with sub-cellular resolution.

Figure 13A:
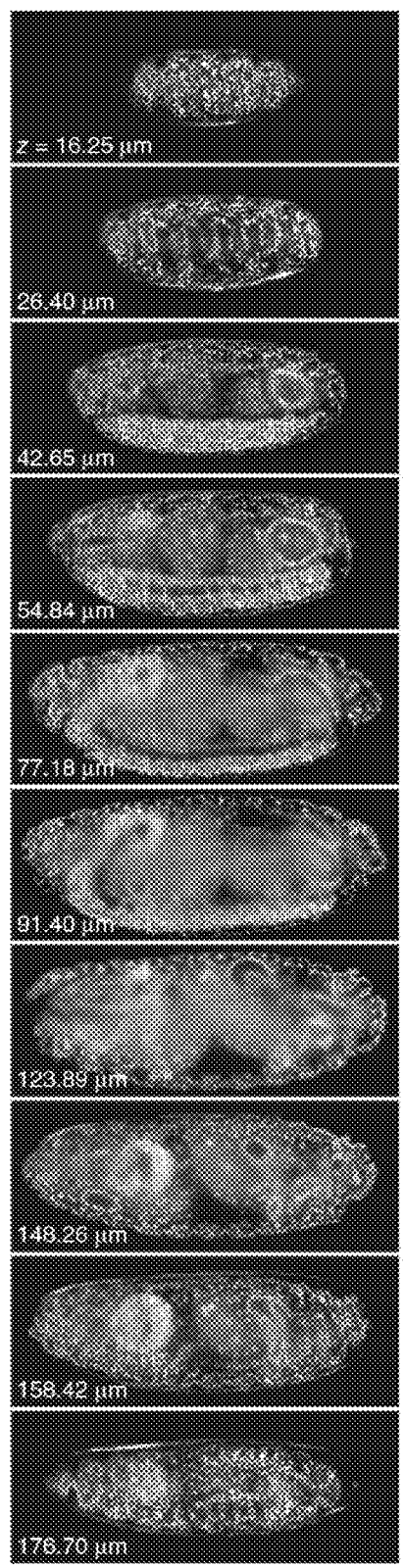
FIG. 13A are images of fluorescence taken with the microscope system of FIG. 1A at steps along the detection axis using a one photon excitation scheme on a *Drosophila* embryo as the biological specimen.

Referring to FIG. 13A, optical slices from a simultaneous multiview in vivo recording of a nuclei-labeled stage 16 *Drosophila* embryo (dorsal side up) are obtained with one-photon excitation using the microscope system 100. A stage 16 embryo is an embryo that has undergone a certain number of development cycles (such as cell division or mitoses) and is currently in the middle of a particular development cycle. The slices are taken along image planes at distinct values of z; for example, the images that are shown in FIG. 13A are taken at the following values for z (starting from the top of the page) z=16.25 µm, 26.40 µm, 42.65 µm, 54.84 µm, 77.18 µm, 91.40 µm, 123.89 µm, 148.26 µm, 158.42 µm, and 176.70 µm. In all, many more images are recorded for a single specimen 101. For example, about 100 images can be recorded in steps on the order of a micrometer (for example, 2.03 µm). The depicted slices in FIG. 13A represent only a small subset of the total number of slices recorded across the volume of the specimen 101.

Figure 13C:
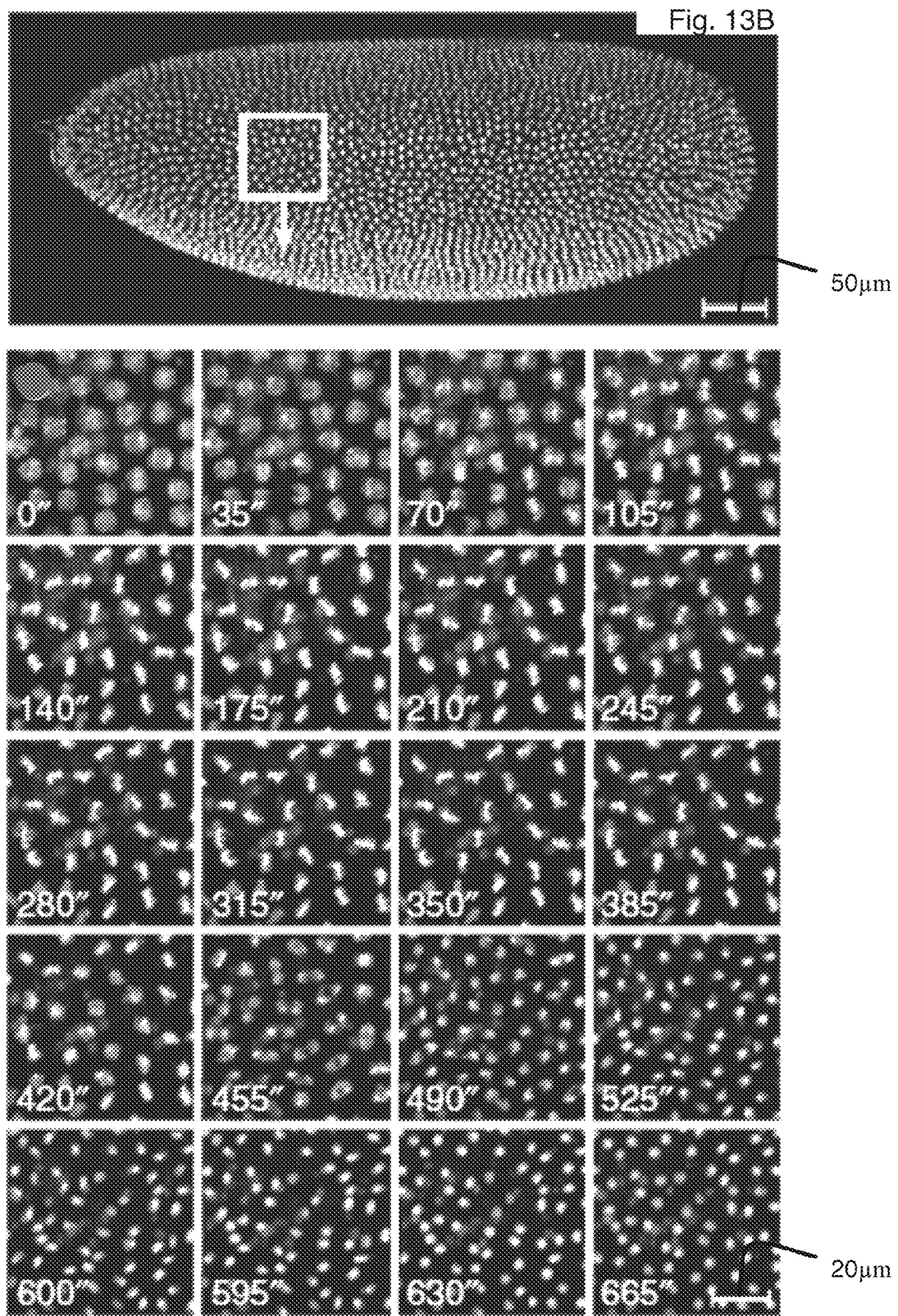
FIG. 13C are images of one region of the *Drosophila* embryo of FIG. 13B taken in a time lapse series during the thirteenth mitotic cycle of development.
Figure 13D:
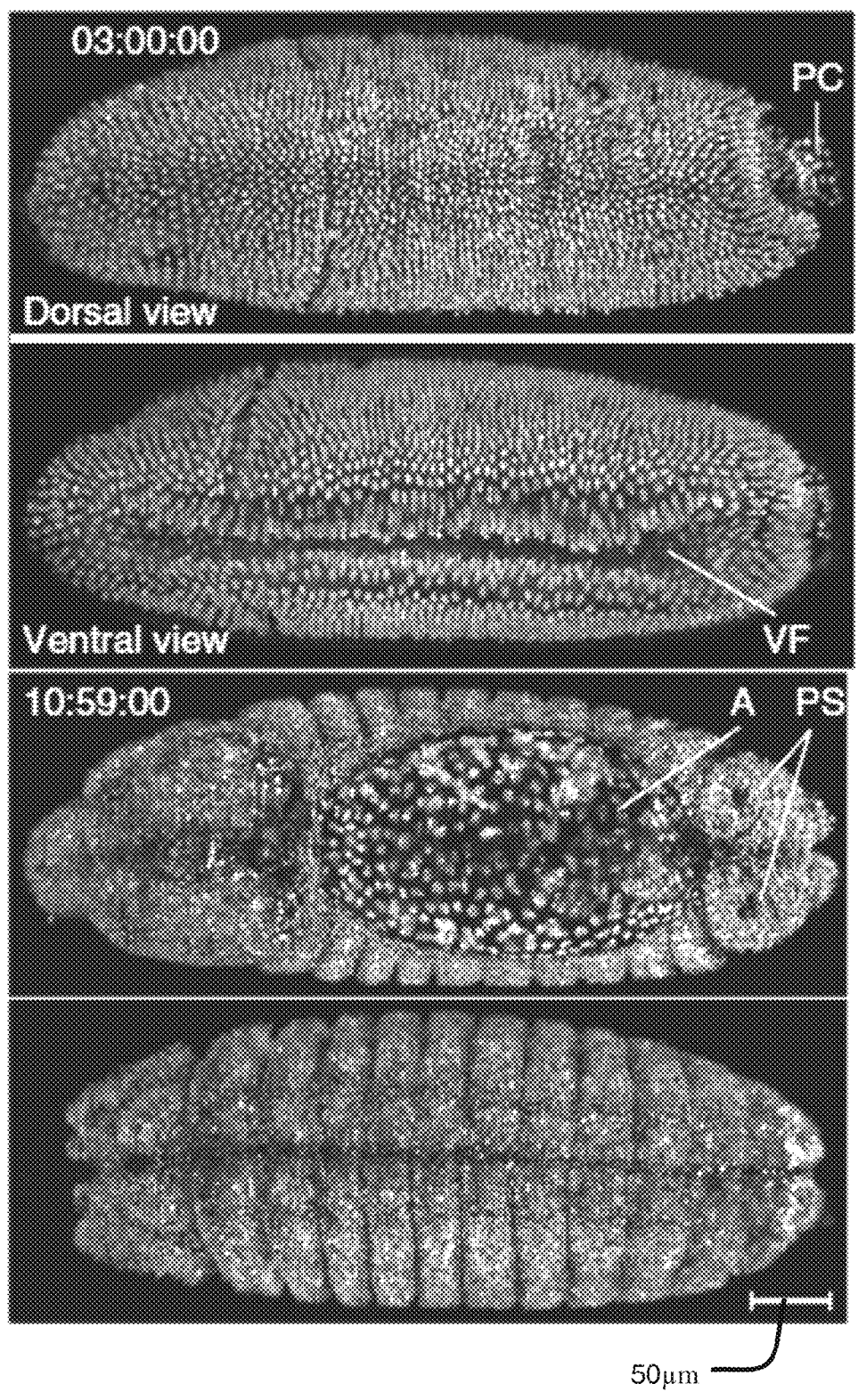
FIG. 13D are maximum-intensity projections of the images of the fluorescence obtained during one-photon excitation using the microscope system of FIG. 1A on the *Drosophila* embryo of FIGS. 13A-13C.

FIG. 13B shows a maximum-intensity projection of a recording of a stage 5 Drosophila embryo obtained with one-photon excitation using the microscope system 100. The white rectangle indicates the region corresponding to the time series shown below the projection, and is located in the transition region between two optical views. FIG. 13C shows the time-series of the nuclear dynamics during the thirteenth mitotic cycle of the rectangular region of FIG. 13B. The nuclear dynamics are quantitatively resolved in the entire embryo by one-photon excitation using the microscope system 100. FIG. 13D shows maximum-intensity projections of the images of the fluorescence obtained during one-photon excitation using the microscope system 100 on the *Drosophila* embryo. Separate projections are shown for dorsal and ventral halves of the fused and background-corrected three-dimensional image stacks. The embryo was recorded in 30-second intervals, using an acquisition period of 15 seconds per time point. The complete recording comprises one million images (11 terabytes) for about 2,000 time points recorded from 3 to 18.5 hours post fertilization. The reference to PC indicates pole cells, the reference to VF indicates a ventral furrow, the reference to A indicates amnioserosa, and the reference to PS indicates posterior spiracles. The scale bars are shown for example only.

Figure 14A:
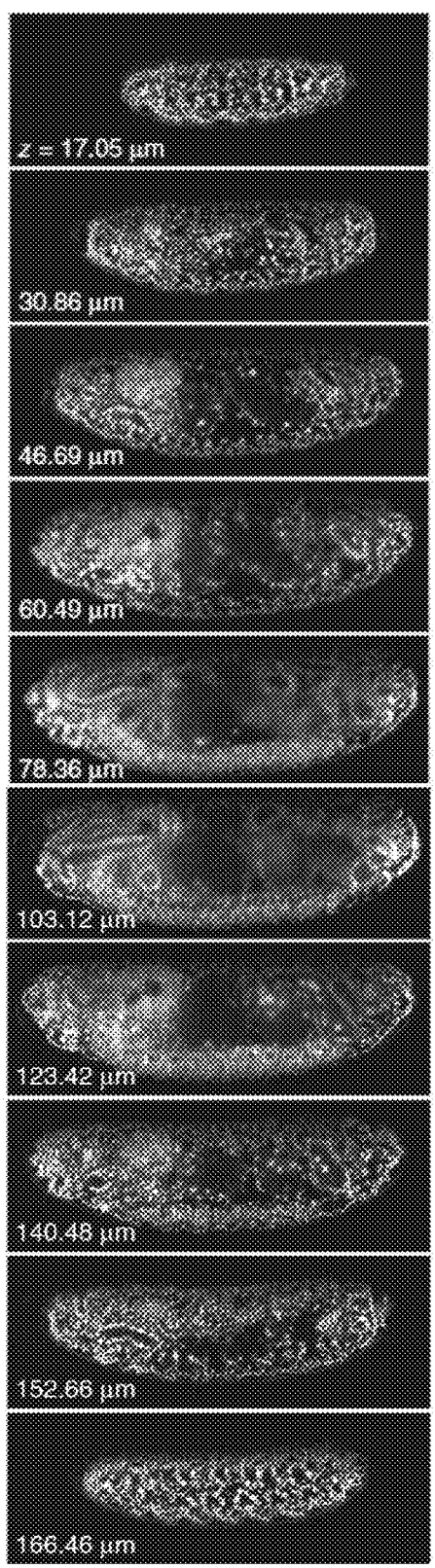
FIG. 14A shows images of a *Drosophila* embryo taken at exemplary imaging planes along the detection axis with the microscope system of FIG. 1A using a two-photon excitation scheme.

Referring to FIG. 14A, optical images are taken with the microscope system 100 of in vivo recording of a nuclei-labeled stage 16 *Drosophila* embryo (dorsal side up) using a two-photon excitation scheme. The slices in this example are taken along image planes at distinct values of z; for example, the images of the embryo that are shown in FIG. 14A are taken at the following values for z (starting from the top of the page) z=17.05 µm, 30.86 µm, 46.69 µm, 60.49 µm, 78.36 µm, 103.12 µm, 123.42 µm, 140.48 µm, 152.66 µm, and 166.46 µm. In all, many more images can be recorded for a single specimen 101. For example, about 100 images can be recorded in steps on the order of a micrometer (for example, 2.03 µm). The depicted slices in FIG. 14A represent only a small subset of the total number of slices recorded across the volume of the specimen 101.

Figure 14B:
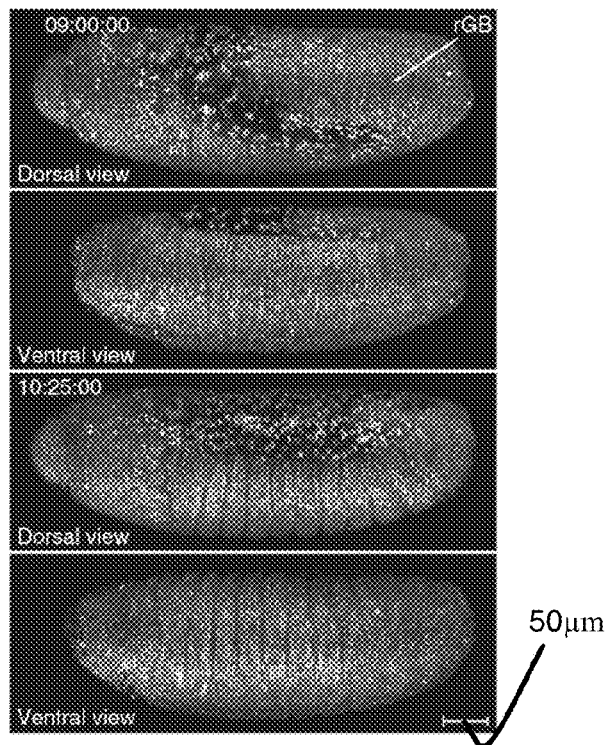
FIGS. 14B and 14C show maximum-intensity projections of a time-lapse recording of *Drosophila* embryonic development taken with the microscope system of FIG. 1A using the two-photon excitation scheme of FIG. 14A.
Figure 14C:
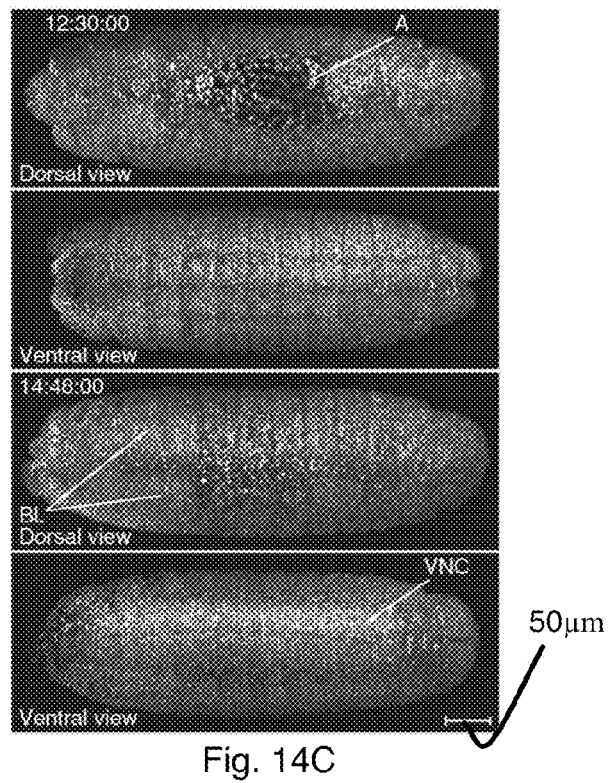

FIG. 14B shows the maximum-intensity projections of a time-lapse recording of *Drosophila* embryonic development taken with the microscope system 100 using a two-photon excitation scheme. Separate projections are shown for dorsal and ventral halves of the fused three-dimensional image stacks. The entire embryo was recorded in 30-second intervals over a period of 2 hours during germ band retraction, using an acquisition period of 20 seconds per time point. The complete recording comprises 37,620 high-resolution images (387 gigabytes). FIG. 14C shows the maximum-intensity projections of a time-lapse recording of Drosophila embryonic development taken with the microscope system 100 using a two-photon excitation scheme. The entire embryo was recorded in 30-second intervals over a period of 3 hours during dorsal closure and ventral nerve cord formation, using an image acquisition period of 20 seconds per time point. The complete recording comprises 68,460 high-resolution images (705 gigabytes). In the images, the term rGB refers to a retracting germ band, the term A refers to amnioserosa, the term VNC refers to a ventral nerve cord, and the term BL refers to brain lobes. Scale bars are shown for example only.

As evident from these images, the recording is free of the spatial and temporal artifacts intrinsic to sequential multiview imaging, and provides excellent temporal sampling of nuclei movements, characteristics that enable comprehensive nuclei tracking in the syncytial blastoderm.

The one-photon excitation scheme (results of which are shown in FIGS. 13A-D) provides an excellent signal-to-noise ratio for small penetration depths but was less able to capture structures deep inside the embryo. In contrast, the two-photon excitation scheme (results of which are shown in FIGS. 14A-C) has reduced autofluorescence when compared with the one-photon excitation scheme and provided near complete physical coverage of the embryo even for late developmental stages. The two-photon excitation scheme can require longer exposure times than the one-photon excitation scheme because of the potentially lower signal rate when using two-photon excitation.

A temporal resolution of 30 seconds for the whole embryo was obtained using the two-photon excitation scheme, and it captured global cellular dynamics during germ band retraction, dorsal closure, and ventral nerve cord formation.

Cell Tracking in *Drosophila* Embryos

Cell tracking in entire developing *Drosophila* embryos has so far been technically challenging. Although there are impressive quantitative studies of cell behavior, existing methods are limited to partial spatial observations and rely on time-consuming semi-automated approaches to image processing, which may be scaled to analyze the full embryo.

Figure 15B:
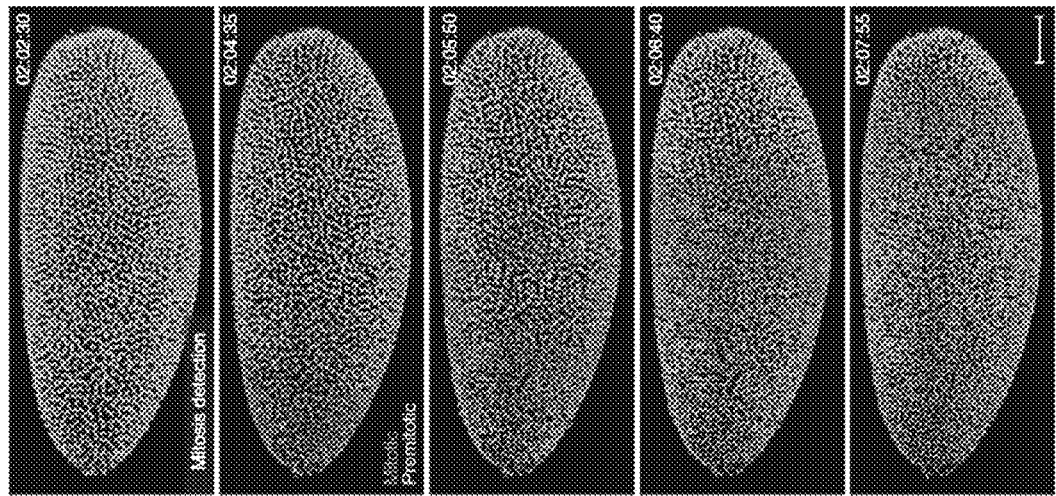
FIG. 15B shows images of the cell-tracked *Drosophila* embryo of FIG. 15A taken with the microscope system of FIG. 1A as the thirteenth mitotic wave progresses through the *Drosophila* embryo.
Figure 15A:
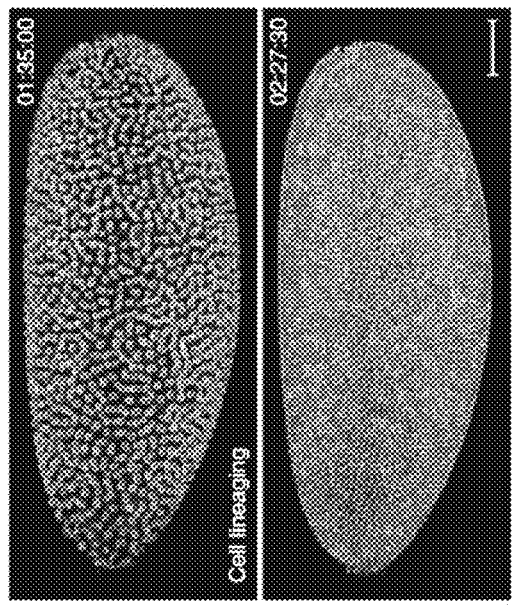
FIG. 15A shows raw image data superimposed with cell tracking results of an entire *Drosophila* embryo taken before the twelfth mitotic wave and after the thirteenth mitotic wave using the microscope system of FIG. 1A.
Figure 15C:
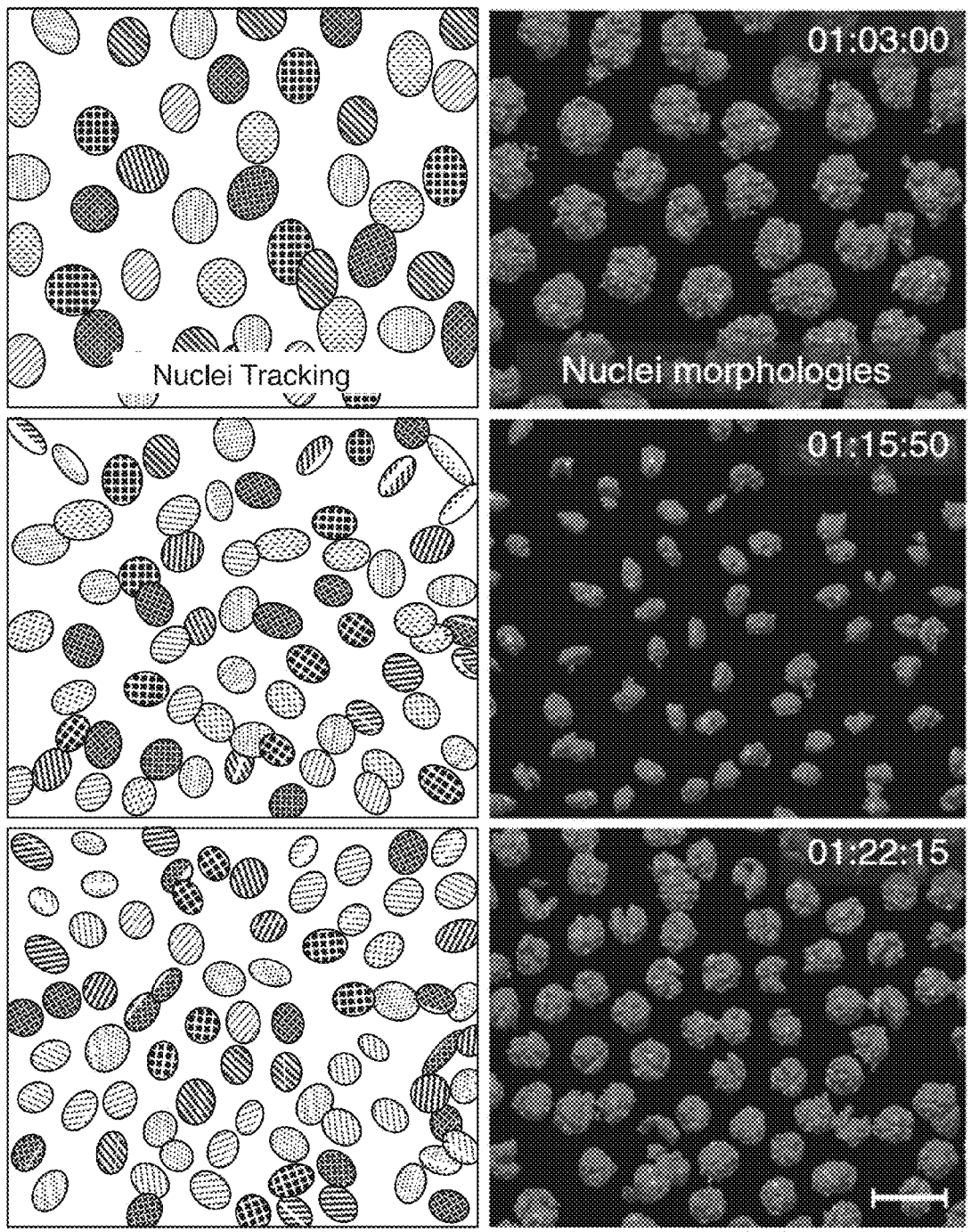
FIG. 15C shows an enlarged view of a reconstructed *Drosophila* embryo of FIG. 15A with cell tracking information on the left and morphological nuclei segmentation on the right taken with the microscope system of FIG. 1A.
Figure 15D:
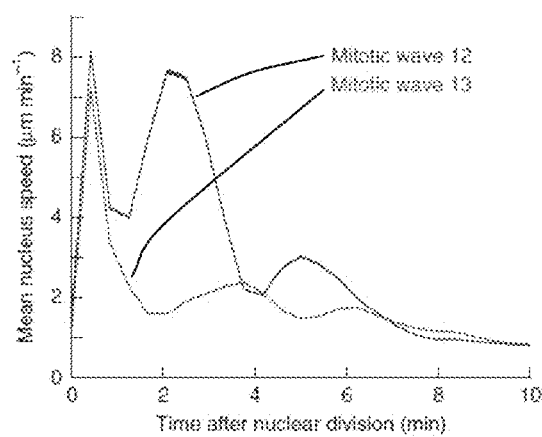
FIG. 15D shows a graph of the average nucleus speed as a function of time after nuclear division within the *Drosophila* embryo of FIGS. 15A-15C.
Figure 15E:
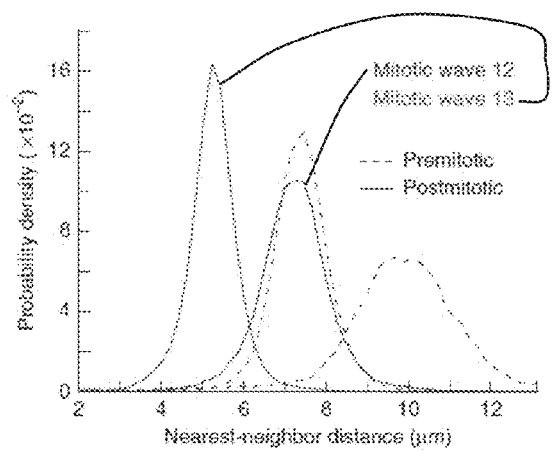
FIG. 15E shows a graph of the distribution of the distances between nearest nuclei neighbors within the *Drosophila* embryo of FIGS. 15A-15C.

Referring to FIGS. 15A-E, in addition to basic imaging, the microscope system 100 enables cell tracking in the entire *Drosophila* embryo. As shown in FIG. 15A, global nuclei tracking in the entire *Drosophila* syncytial blastoderm is produced from raw image data from a video that were superimposed with automated tracking results using a sequential Gaussian mixture model approach. Images show snapshots before the twelfth mitotic wave and after the thirteenth mitotic wave, using a random color scheme in the first time point, which is propagated to daughter nuclei using tracking information. As shown in FIG. 15B, global detection of nuclear divisions during the thirteenth mitotic wave in the *Drosophila* syncytial blastoderm is shown; non-dividing nuclei are shown in cyan and dividing nuclei are shown in magenta. The color of dividing nuclei progressively fades back to cyan within five time points. FIG. 15C shows an enlarged view of a reconstructed embryo with nuclei tracking information on the left and morphological nuclei segmentation on the right. The nuclei tracking information is generated from a random color scheme (which is converted into a random pattern scheme in black and white). FIG. 15D shows the average nucleus speed as a function of time after nuclear division. Values at t=0 represent all pre-mitotic nuclei. Values at t greater than 0 represent post-mitotic nuclei at time t after mitosis. The small standard error of the mean (or s.e.m.) (equal to or smaller than line thickness) arises from the large specimen size of ~2,500-5,000 specimens per time point. FIG. 15E shows the distribution of the distances between nearest nuclei neighbors. Mean and standard deviation of the post-mitotic distributions are 7.57±1.34 μm ($12^{th}$ wave; n=1.44×$10^5$) and 5.52±0.99 μm ($13^{th}$ wave; n=4.66×$10^5$).

By taking advantage of the improved spatio-temporal resolution, *Drosophila* embryo cell nuclei can be successfully reconstructed and tracked through multiple division cycles in the entire syncytial blastoderm using the microscope system 100. The nuclei can be tracked through the $12^{th}$ and $13^{th}$ mitotic waves, which represent some of the fastest global processes in the embryo. Nuclei were detected automatically with an accuracy of 94.74%±0.68% with respect to false positives (for those detected, but that are not present) and almost 100% with respect to false negatives (for those not detected), as evaluated by the human expert. The segmentations were obtained using two independent methods: an efficient implementation of the Gaussian Mixture Model (GMM), which provides nuclear positions and size estimates (as shown in FIGS. 15A and B), and a three-dimensional implementation of the diffusion gradient vector field algorithm, which yields full nuclear morphologies (as shown in FIG. 15C). The GMM-based segmentation and tracking was implemented on a GPU, which permitted reconstruction of nuclei dynamics in the entire embryo in only 40 seconds per time point.

Owing to the high temporal resolution in the simultaneous multiview light sheet microscope system 100, it was sufficient to initialize each time point with the mixture model from the previous time point in order to obtain tracking information. This approach yielded a tracking accuracy between frames of 98.98%±0.42%. To follow nuclei through their division, a machine learning classifier was trained based on local image features. This approach yielded a nuclei division detection and linkage accuracy of 93.81%±2.71% throughout the recording. Three distinct types of motion are quantified: global nuclei displacements, synchronized waves of nuclear division, and fast local nuclei displacements (daughter nuclei separating after division).

The results are summarized in FIGS. 15D and E. The quantitative analysis of mitotic waves reveals that average nucleus movement speeds are highest directly after nuclear division (8.12±2.59 μm/min in $12^{th}$ wave and 7.21±2.21 μm/min in $13^{th}$ wave, mean±s.d.; n=2,798 and 4,852, Huber robust estimator) and exhibit two pronounced local maxima at 2.1 and 5.0 minutes after division ($12^{th}$ wave; 3.8 and 6.3 min for $13^{th}$ wave), which relate to the relaxation process of the global nuclei population towards a new packing pattern (FIG. 15D). The average distance between daughter nuclei reaches a maximum 1.25 minutes ($12^{th}$ wave) and 1.67 minutes ($13^{th}$ wave) after division, which is almost two-fold higher than the global average nearest neighbor distance in the embryo (7.57±1.34 μm in $12^{th}$ wave and 5.52±0.99 μm in $13^{th}$ wave, mean±s.d.; n=1.44×$10^5$ and 4.66×$10^5$, Huber robust estimator), and relaxes to 8.76 μm for mitotic wave 12 and to 5.68 μm for mitotic wave 13, owing to the almost two-fold increase in nuclei count by the end of each mitotic wave.

Determination of nuclei positions, nuclei sizes and nuclei tracking were performed within the computational system 190 by modeling each image as a mixture of Gaussians and sequentially estimating the mixture parameters across time. Approximating nuclear shape intensity by a Gaussian provides a good trade-off between model complexity and shape information. In particular, each image can be modeled as:

$$I(x, y, z) \propto \sum_{k=1}^{K} \pi_k N\left((x, y, z); \mu_k, \sum_k\right),$$

where K is the number of objects in the image, $\mu_k$ is the center location of each nucleus, $\Sigma_k$ is the covariance matrix (representing the shape of each nucleus as an ellipsoid), and $\pi_k$ is the relative intensity. Given each image as an input, these parameters can be estimated in a maximum-likelihood framework using, for example, Expectation-Maximization algorithm.

Due to the fine temporal resolution and excellent spatial coverage achieved by the simultaneous multiview light-sheet microscope system 100, we used each solution from time $T_{i-1}$ as an initialization for time point $T_i$. Given that each Gaussian in an image derives from a Gaussian in the previous time point, tracking information can be directly recovered. To handle cell divisions, a set of examples with cells dividing and cells not dividing is collected, a machine learning classifier is trained based on local image features.

The tracking using Gaussian mixture models was implemented on a graphics processing unit (GPU) and can be implemented using CUDA™, which increases computing performance (and can result in a 100× speed-up), which permits the processing of nuclear positions and movements in the entire embryo with thousands of nuclei and millions of voxels in only 40 seconds per time point, using a processing workstation with a single Tesla GPU (Nvidia Corporation).

*Drosophila* Neural Development

Referring to FIGS. 16A-G, the microscope system 100 is used to investigate neuron type specification and axonal guidance in the *Drosophila* nervous system. Neuro-developmental dynamics are often studied by comparing fixed specimens at different developmental stages, but also by live imaging in a local context. The microscope system 100 can record and image data on the developmental dynamics of the entire embryonic nervous system.

Figure 16A:
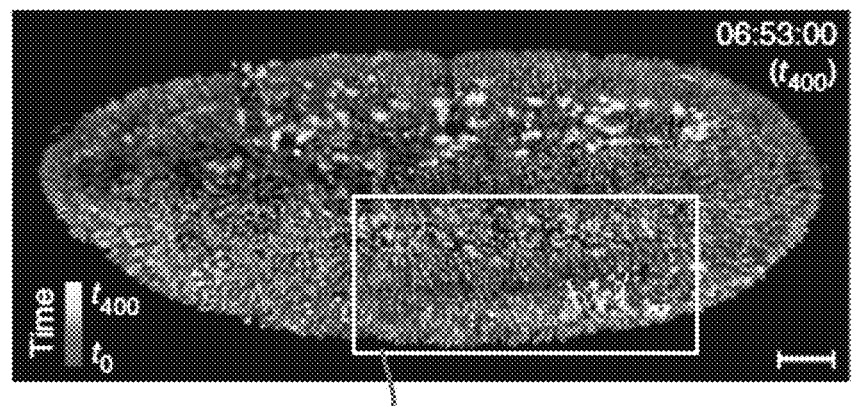
FIG. 16A shows an image obtained using the microscope system of FIG. 1A in a one-photon excitation scheme on a histone-labeled *Drosophila* embryo, superimposed with manually reconstructed lineages of three neuroblasts and one epidermoblast for 120-353 minutes post fertilization.
Figure 16B:
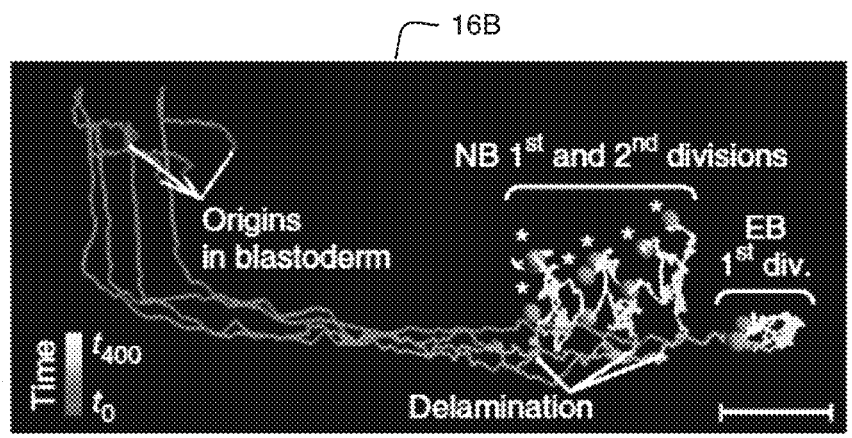
FIG. 16B shows an enlarged view of the tracks highlighted in FIG. 16A.

FIG. 16A shows the results of imaging using the microscope system 100 in a one-photon excitation scheme of a histone-labeled *Drosophila* embryo as the specimen 101, superimposed with manually reconstructed lineages of three neuroblasts and one epidermoblast for 120-353 minutes post fertilization (time points 0-400). The track color shown encodes time and the scale bar corresponds to 30 μm. FIG. 16B shows the enlarged view of the tracks highlighted in FIG. 16A. The green spheres show cell locations at the time point 400. The asterisks mark six ganglion mother cells produced in two rounds of neuroblast division. The term NB refers to a neuroblast and the term EB refers to an epidermoblast.

Figure 16C:
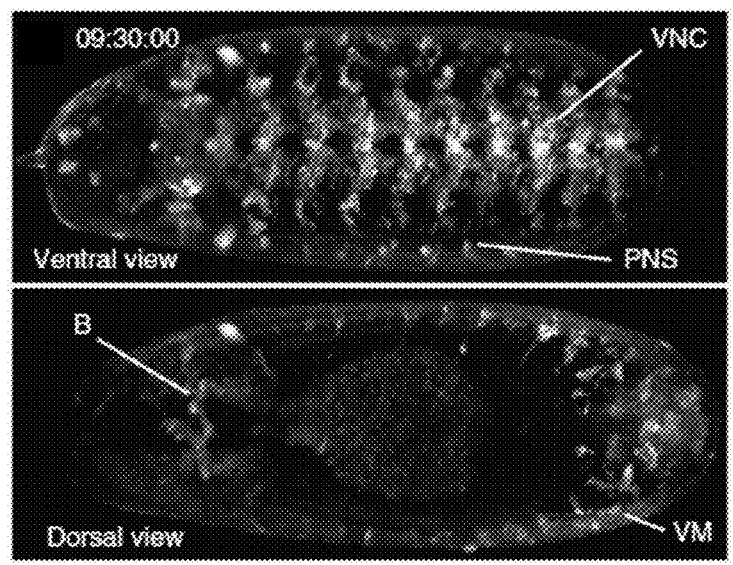
FIGS. 16C-E show maximum-intensity projections (dorsal and ventral halves) of *Drosophila* embryonic nervous system development, recorded with the microscope system of FIG. 1A using a one-photon excitation scheme.
Figure 16D:
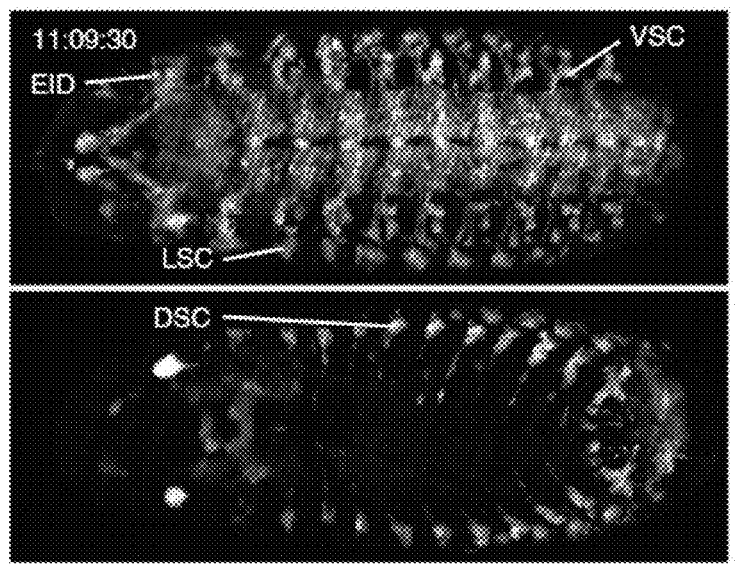
Figure 16E:
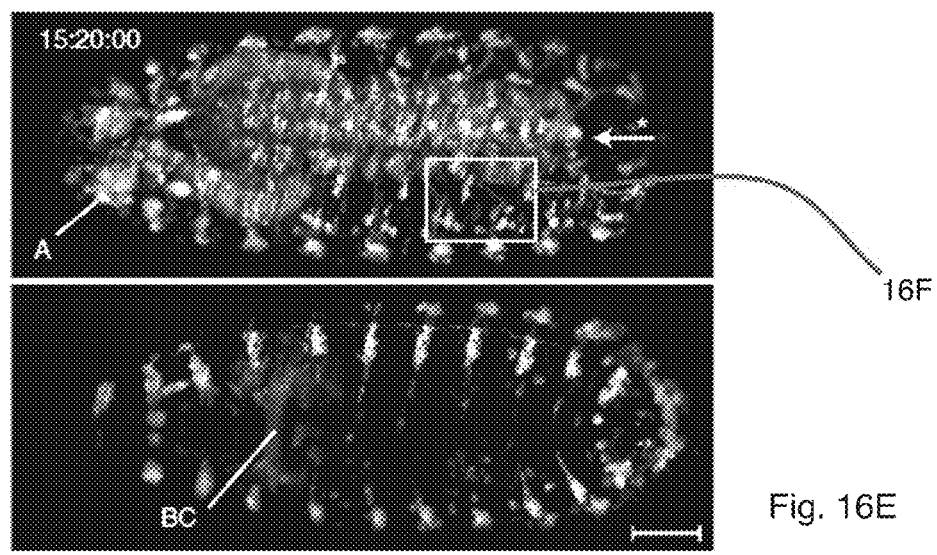

FIGS. 16C-E show maximum-intensity projections (dorsal and ventral halves) of *Drosophila* embryonic nervous system development, recorded with the microscope system using a one-photon excitation scheme. The *Drosophila* (for example, elav(C155)-GAL4,UAS-mCD8::GFP transgenic) embryo was recorded in 30-second intervals over the period 9.5-15.3 hours post fertilization (about 700 time points), using an image acquisition period of 15 seconds per time point. The intensity normalization was performed within the computational system 190 to compensate for GFP signal increase over time. The autofluorescent vitelline membrane was computationally removed in FIG. 16C.

Figure 16F:
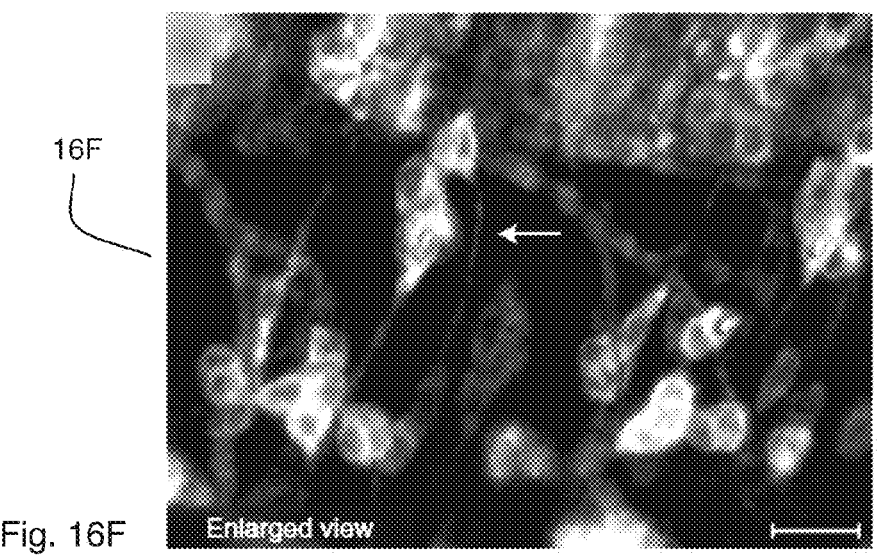
FIG. 16F shows an enlarged view of the area highlighted in FIG. 16E.
Figure 16G:
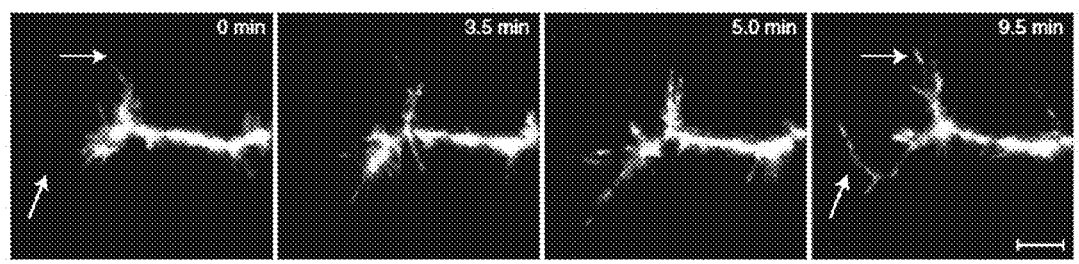
FIG. 16G shows a progression of maximum-intensity projections of axonal morphogenesis in a *Drosophila* transgenic embryo (false color look-up-table), recorded with the microscope system of FIG. 1A using a one-photon excitation scheme.

FIG. 16F shows an enlarged view of the area highlighted in FIG. 16E. FIG. 16G shows a progression of maximum-intensity projections of axonal morphogenesis in a Ftz-ng-GAL4, 10XUAS-IVS-myr:: GFP transgenic embryo (false color look-up-table), recorded with the microscope system 100 using a one-photon excitation scheme. The images represent a 0.3% sub-region of the total covered volume. The term VNC refers to the ventral nerve cord, the term PNS refers to the peripheral nervous system, the term B refers to the brain, the term VM refers to the vitelline membrane, the term EID refers to the eye-antennal imaginal disc, the term VSC refers to the ventral sensory cells, the term LSC refers to the lateral sensory cells, the term DSC refers to the dorsal sensory cells, the term A refers to the antenna, the term BC refers to brain commissure. The asterisk indicates shortening of the VNC. The scale bars that are shown are provided as examples, and are as follows: In FIGS. 16A and 16B, the bars are 30 µm in length; in FIGS. 16C-E, the bars are 50 µm in length; in FIG. 16F, the bar is 10 µm in length; and in FIG. 16G, the bar is 5 µm.

Transgenic embryos expressing elav(C155)-GAL4 and UAS-mCD8:: GFP were used to visualize all post-mitotic neurons, and time-lapse one-photon imaging was performed of the entire embryonic nervous system with 25 and 30 seconds time resolution, capturing neural development in about 400,000 high-resolution images (4 terabytes) for more than 700 time points. Recording a four-view data set of the entire embryo required only 2 mJ of light energy per time point and showed negligible photo-bleaching. The resulting data sets provide detailed information on the development of the central and peripheral nervous systems (See FIGS. 16C-F) and reveal fine details in the dynamics of axonal outgrowth. For instance, the time-lapse recordings show several clusters of abdominal sensory organs (dorsal, lateral and ventral) and the formation of connectives in the ventral nerve cord. Strikingly, the dynamics of these cells across different segments appear to be highly stereotypic, indicating the role of global cues. The imaging also captures the dynamics of sensory cells in the head region and in the posterior segments of the specimen 101. The entire morphogenesis of the eye-antennal imaginal disc can be followed, which separates from the embryonic brain to move in an anterior-medial direction. The antenna anlage separates from the larval eye (Bolwig's organ) as both establish their final locations. It is even possible to follow the morphogenesis of the deeply embedded embryonic brain, which starts as two bilaterally symmetrical neurogenic regions, initially separated from each other, and begins to move posteriorly with head involution. The development of commissures is visible at high temporal resolution.

Additionally, the microscope system 100 performed high-resolution experiments with Ftz-ng-GAL4,10XUAS-IVS-myr:: GFP embryos exhibiting sparse expression in the central nervous system. The spatial sampling is increased by more than a factor of six, maintaining the same high temporal resolution and imaging for the same period of time (30-second intervals for 8.5 hours, providing approximately 460,000 images or 4.6 terabytes of data. These recordings preserve the capability to follow global processes and at the same time reveal detailed filopodial dynamics during axonal morphogenesis at excellent spatio-temporal resolution (See FIG. 16G). For example, the high-speed imaging results show that zones of filopodial extension and exploration are retained proximal from the growth cones for long periods of time.

Additionally, to complement the automated reconstruction of cellular dynamics in early *Drosophila* embryos, the microscope system 100 can be used for cell tracking and cell lineage analyses in later developmental stages of the specimen 101. For example, using a two-photon excitation scheme, manual cell tracking can be performed in non-superficial layers of the retracting germ band. In addition, neuroblast and epidermoblast lineages can be followed in a one-photon excitation scheme. The high signal-to-noise ratio of the one-photon data permitted the tracking of blastoderm cells through gastrulation and subsequent cell divisions for a total period of 400 time points (approximately 4 hours; as shown in FIGS. 16A and B). These reconstructions capture cellular dynamics in the early stages of nervous system development, including neuroblast delamination and birth of the first ganglion mother cells.

The computational system 190 performs specific actions to enable the acquisition of the morphologies of the nuclei within the specimen 101. In particular, an image I(x,y,z) that is created by the computation system 190 is segmented by simulating the fluorescence intensities as attractive forces (f) embedded in a medium governed by fluid flow equations. A gradient vector field v(x,y,z)=[u(x,y,z), v(x,y,z), w(x,y,z)] can be defined as the field that minimizes the functional, $$\epsilon = \iiint \mu(u_x^2 + u_y^2 + u_z^2 + v_x^2 + v_y^2 + v_z^2 + w_x^2 + w_y^2 + w_z^2) + |\nabla f|^2 |v - \nabla f|^2 dxdydz \text{ tm} \quad (1)$$

where, $$f = \nabla |G_\sigma(x,y,z) * I(x,y,z)|^2 \quad (2)$$

and where $G_\sigma(x, y, z)$ represents a three-dimensional Gaussian with standard deviation $\sigma$ and * denotes convolution. Briefly, using the calculus of variations we obtain a set of Euler equations, which can be solved by treating u, v and w as functions of time, $$u_t(x,y,z,t) = \mu \nabla^2 u(x,y,z,t) - (u(x,y,z,t) - f_x(x,y,z)) \times (f_x(x,y,z)^2 + f_y(x,y,z)^2 + f_z(x,y,z)^2) \quad (3)$$

$$v_t(x,y,z,t) = \mu \nabla^2 v(x,y,z,t) - (v(x,y,z,t) - f_y(x,y,z)) \times (f_x(x,y,z)^2 + f_y(x,y,z)^2 + f_z(x,y,z)^2) \quad (4)$$

$$w_t(x,y,z,t) = \mu \nabla^2 w(x,y,z,t) - (w(x,y,z,t) - f_z(x,y,z)) \times (f_x(x,y,z)^2 + f_y(x,y,z)^2 + f_z(x,y,z)^2) \quad (5)$$

The steady-state solution of these linear parabolic equations is the solution of the Euler equations and yields the required flow field. The regularization parameter µ balances the diffusive (first term) vs. the advective (second term) components in Eq. (1), that is, it determines the amount of smoothing exerted by the algorithm, and should be increased in the presence of noise.

The gradient field calculation is followed by gradient flow tracking, in which similar groups of voxels were identified as those that "flow" towards the same sink. This generates a "mosaic" image, in which each tile (the basin of one sink) contains only one object. The segmentation was finalized by adaptively thresholding each tile. The computational system 190 calculates the optimum threshold separating the two classes, fore- and background, so that their combined intraclass variance is minimal (Otsu's method). Voxels with values smaller than this threshold were considered background.

The high temporal resolution of the recordings enabled the initialization of the diffusion gradient vector field segmentation algorithms, for a time point $T_i$, with the solution that converged in $T_{i-1}$. This resulted in more than 20× convergence speed-up, and was essential to obtain high-quality shape information and making the algorithm practical for large 4D datasets.

The data sets that are stored within the computational system 190 and processed to create the image (716) are large in size (for example, they can typically in the order of up to dozens of terabytes). When routinely working with these data sets, the operator of the microscope system 100 can select spatial and temporal subsets of the images, and/or only image frames that originate from a specific color channel, view angle, specimen, or camera 106, 108. If this is done, then the computational system 190 can store and run a separate program that facilitates the organization, browsing, and processing of the images in a way that is convenient, fast, extensible, and with minimal network and I/O load. To this end, such a computer program can implement the following concepts: (a) virtual folders; by which the user can make sophisticated data subset selections, (b) processing task definition is separated from data selection (for re-use and documentation), (c) a plug-in system, for the easy implementation of custom processing code, (d) connection to external programs Vaa3D and ImageJ, and (e) a convenient graphical user interface for defining the virtual folders and processing tasks, as well as for browsing through data sets (for viewing the images and their associated meta information).

In summary, a complete technology framework has been described that provides for light sheet-based one-photon and multi-photon simultaneous multiview imaging and image analysis, which overcomes the limitations of sequential multiview strategies and enables quantitative systems-level imaging of fast dynamic events in large living specimens. The framework provides near-complete physical coverage through the acquisition of a plurality of complementary optical views with a maximum time shift of 20 milliseconds, independent of specimen size. Temporal correspondence of complementary views is improved by more than three orders of magnitude and imaging speed is improved more than 20-fold over light sheet microscopy with sequential four-view imaging. The system is designed for high-speed long-term imaging under physiological conditions, using real-time electronics and an advanced computational infrastructure for sustained data acquisition at 350 megabytes $s^{-1}$ (175 million voxels per second) for up to several days. The system includes computational solutions for high-throughput multiview image fusion and image data management of experiments, which typically comprise millions of high-resolution images and up to several dozens of terabytes per specimen.

Other implementations are within the scope of the following claims.

For example, in other implementations, the light sheets 102, 104 produced within the illumination subsystems 112, 114 can be produced with a static arrangement and thus can be static light sheets. For example, the optical components 132, 134 can include a telescope lens pair and a cylindrical lens that focuses the light along only one direction.

The light sources 122, 124 can include a pulsed Ti:Sapphire laser (such as a Chameleon Ultra II by Coherent, Inc. of Santa Clara, Calif.). An additional module can be placed between the light sources 122, 124 and the respective optical component set 132, 134. The additional module can modify the output of the light sources 122, 124 and can provide laser intensity modulation and IR beam splitting. The module consists of a beam attenuation sub-module (for example, an AHWP05M-980 mounted achromatic half-wave plate and GL10-B Glan-laser polarizer by Thorlabs Inc. of Newton, N.J.), a Pockels cell with driver (such as a Model 350-80-LA-02 KD*P series electro-optic modulator and a Model 302RM driver by Conoptics Inc. of Danbury, Conn.) and an IR beam splitter (such as a broadband polarizing cube beam splitter such as model PBSH-450-2000-100 by Melles Griot and an achromatic ½ wave plate such as model WPA1312-2-700-1000 by Casix, Inc. of China).

What is claimed is:

1. A method of imaging a live biological specimen using a microscope, the method comprising:
    generating a plurality of light sheets;
    directing the plurality of light sheets along an illumination axis through the biological specimen such that the light sheets spatially and temporally overlap within the biological specimen along an image plane, and optically interact with the biological specimen within the image plane; and
    recording, at each of a plurality of views, images of the fluorescence emitted along a detection axis from the biological specimen due to the optical interaction between the light sheets and the biological specimen;
    wherein the temporal overlap is within a time shift that is less than a resolution time that corresponds to a spatial resolution limit of the microscope.

2. The method of claim 1, further comprising creating an image of the biological specimen by:
    for each view of the plurality of views:
        registering the images of the recorded fluorescence; and
        fusing the registered images into a fused image;
    registering each of the fused images of all of the plurality of views; and
    fusing the registered fused images into a final image representative of the image plane of the biological specimen that corresponds to the spatial and temporal overlap of the light sheets within the biological specimen.

3. The method of claim 2, wherein:
    registering the recorded fluorescence images comprises aligning the images of the recorded fluorescence; and
    fusing the registered images comprises combining the registered images into a single image.

4. The method of claim 1, further comprising:
    translating one or more of the biological specimen, the plurality of light sheets, and the plurality of views at which the fluorescence is recorded relative to each other along a linear axis by incremental steps so that the plurality of light sheets spatially and temporally overlap within the biological specimen along a set of image planes that spans at least a portion of the biological specimen; and
    for each image plane, recording, at the plurality of views, fluorescence produced by the biological specimen due to the optical interaction between the light sheets and the biological specimen.

5. The method of claim 4, wherein the linear axis is aligned with the detection axis.

6. The method of claim 4, wherein translating one or more of the biological specimen, the plurality of light sheets, and the plurality of recording views relative to each other along the linear axis by incremental steps comprises:
    maintaining the position of the plurality of light sheets and the plurality of recording views; and
    translating the biological specimen along the linear axis.

7. The method of claim 4, wherein translating one or more of the biological specimen, the plurality of light sheets, and the plurality of recording views relative to each other along the linear axis by incremental steps comprises:
maintaining the position of the biological specimen; and
translating the plurality of light sheets and the plurality of recording views along the linear axis.

8. The method of claim 1, wherein recording the images of the fluorescence produced by the biological specimen due to the optical interaction between the light sheets and the biological specimen comprises recording one-photon fluorescence produced by the biological specimen.

9. The method of claim 8, wherein generating each light sheet comprises generating a continuous wave light sheet, the method further comprising:
shuttering the plurality of light sheets so that each light sheet arrives at a distinct point in time at the biological specimen but still within the temporal overlap.

10. The method of claim 1, wherein recording the images of the fluorescence produced by the biological specimen due to the optical interaction between the light sheets and the biological specimen comprises recording two-photon fluorescence produced by the biological specimen.

11. The method of claim 10, wherein generating each light sheet comprises generating a pulsed wave light sheet, and directing the plurality of light sheets along the illumination axis through the biological specimen such that the light sheets spatially and temporally overlap within the specimen along the image plane comprises activating the light sheets in synchrony.

12. The method of claim 1, wherein recording at the plurality of views comprises recording along the detection axis that is perpendicular to the illumination axis.

13. The method of claim 1, wherein the resolution time corresponds to spatial displacements in the structure of the biological specimen that are on the order of the spatial resolution limit of the microscope.

14. The method of claim 1, wherein a minimal thickness of each of the light sheets taken along the detection axis is less than a cross sectional size of a structure within the specimen to be imaged.

15. A method of imaging a live biological specimen using a light sheet microscope, the method comprising:
generating a plurality of light sheets;
directing the plurality of light sheets along an illumination axis through the biological specimen such that the light sheets spatially and temporally overlap within the biological specimen along an image plane;
recording, at a plurality of views, images of the fluorescence produced by the biological specimen due to the interaction between the biological specimen and the light sheets; and
creating an image of the biological specimen by:
for each view of the plurality of views:
aligning the recorded images; and
combining the aligned images into a fused image;
aligning the fused images from all of the plurality of views; and
combining the aligned fused images into a final image representative of the image plane of the biological specimen that corresponds to the spatial and temporal overlap of the light sheets within the biological specimen.

16. The method of claim 15, wherein a minimal thickness of each of the light sheets taken along a z axis, which is perpendicular to the illumination axis and overlaps the illumination axis along which the fluorescence is recorded, is less than a cross sectional size of a structure within the specimen to be imaged.

17. The method of claim 15, wherein:
recording the images of the fluorescence produced by the biological specimen due to the optical interaction between the light sheets and the biological specimen comprises recording two-photon fluorescence produced by the biological specimen; and
generating each light sheet comprises generating a pulsed wave light sheet, and directing the plurality of light sheets along the illumination axis through the biological specimen such that the light sheets spatially and temporally overlap within the specimen along the image plane comprises activating the light sheets in synchrony.

18. The method of claim 1, wherein recording, at each of the plurality of views, images of the fluorescence emitted along the detection axis comprises recording the images at a plurality of detection subsystems of the microscope, each detection subsystem including a camera and detection optical devices and each detection subsystem being positioned along each of the views.

19. The method of claim 1, wherein generating the plurality of light sheets comprises generating each light sheet from an illumination subsystem of the microscope, each illumination subsystem comprising a light source that produces a light sheet.

20. The method of claim 19, wherein directing the plurality of light sheets along the illumination axis comprises directing the produced light sheets through a set of illumination optical devices toward the biological specimen.

21. The method of claim 1, further comprising mounting the biological specimen to a specimen holder of the microscope.

* * * * *